United States Patent
Ono

(10) Patent No.: US 11,903,646 B2
(45) Date of Patent: Feb. 20, 2024

(54) OPHTHALMIC APPARATUS, METHOD OF CONTROLLING THE SAME, METHOD OF OPHTHALMIC OPTICAL COHERENCE TOMOGRAPHY, AND RECORDING MEDIUM

(71) Applicant: Topcon Corporation, Tokyo (JP)

(72) Inventor: Yusuke Ono, Tokyo (JP)

(73) Assignee: TOPCON CORPORATION, Tokyo (JP)

( * ) Notice: Subject to any disclaimer, the term of this patent is extended or adjusted under 35 U.S.C. 154(b) by 702 days.

(21) Appl. No.: 15/734,237

(22) PCT Filed: Apr. 15, 2019

(86) PCT No.: PCT/JP2019/016099
§ 371 (c)(1),
(2) Date: Dec. 2, 2020

(87) PCT Pub. No.: WO2019/239707
PCT Pub. Date: Dec. 19, 2019

(65) Prior Publication Data
US 2021/0153737 A1     May 27, 2021

(30) Foreign Application Priority Data

Jun. 13, 2018   (JP) ................. 2018-113011

(51) Int. Cl.
*A61B 3/10*        (2006.01)
*G06K 9/78*        (2006.01)
(Continued)

(52) U.S. Cl.
CPC ............ *A61B 3/102* (2013.01); *A61B 3/0025* (2013.01); *G06T 7/0012* (2013.01); *G06T 7/70* (2017.01);
(Continued)

(58) Field of Classification Search
CPC ....... A61B 3/0025; A61B 3/102; A61B 3/152; A61B 3/158; G06T 7/0012; G06T 7/70;
(Continued)

(56) References Cited

U.S. PATENT DOCUMENTS

2008/0055543 A1   3/2008   Meyer et al.
2012/0188555 A1   7/2012   Izatt et al.
(Continued)

FOREIGN PATENT DOCUMENTS

CN   103654721 A   3/2014
JP   2012-61337 A   3/2012
(Continued)

OTHER PUBLICATIONS

Office Action dated Jun. 27, 2023 in Japanese Patent Application No. 2022-174606, 8 pages.
(Continued)

*Primary Examiner* — Jack Dinh
(74) *Attorney, Agent, or Firm* — XSENSUS LLP

(57) ABSTRACT

An ophthalmic apparatus of an embodiment example applies an OCT scan to an anterior segment and constructs an image from acquired data. Further, the ophthalmic apparatus analyzes the image to detect an artifact along an A-scan direction and moves an OCT optical system based on the artifact. Also, the ophthalmic apparatus analyzes the image to detect a corneal image and judges whether an intersection between the artifact and the corneal image is located within a predetermined area. In addition, the ophthalmic apparatus calculates an image quality evaluation value of the image, and controls the OCT optical system to perform an OCT scan of a predetermined pattern if the intersection is located within the area and the image quality evaluation value is equal to or greater than a predetermined threshold.

18 Claims, 11 Drawing Sheets

(51) Int. Cl.
  *G06T 7/00* (2017.01)
  *G06T 7/70* (2017.01)
  *A61B 3/00* (2006.01)

(52) U.S. Cl.
  CPC .............. *G06T 2207/10101* (2013.01); *G06T 2207/30041* (2013.01); *G06T 2207/30168* (2013.01); *G06V 2201/03* (2022.01)

(58) Field of Classification Search
  CPC . G06T 2207/10101; G06T 2207/30041; G06T 2207/30168; G06V 2201/03; G06K 9/78; G06K 2209/05
  See application file for complete search history.

(56) References Cited

U.S. PATENT DOCUMENTS

| | | |
|---|---|---|
| 2012/0288175 A1 | 11/2012 | Iwase et al. |
| 2013/0188140 A1 | 7/2013 | Bagherinia et al. |
| 2015/0085252 A1 | 3/2015 | Fujimura et al. |
| 2015/0245765 A1 | 9/2015 | Fujii et al. |
| 2016/0038021 A1 | 2/2016 | Bagherinia et al. |
| 2016/0345822 A1 | 12/2016 | Fujimura et al. |
| 2017/0251920 A1 | 9/2017 | Tokuda et al. |
| 2017/0358077 A1 | 12/2017 | Xu et al. |

FOREIGN PATENT DOCUMENTS

| | | |
|---|---|---|
| JP | 2012-75641 A | 4/2012 |
| JP | 2012-235835 A | 12/2012 |
| JP | 2013-248376 A | 12/2013 |
| JP | 2015-504740 A | 2/2015 |
| JP | 2015-160103 A | 9/2015 |
| JP | 2016-47094 A | 4/2016 |
| JP | 2017-46976 A | 3/2017 |
| JP | 2017-184874 A | 10/2017 |
| JP | 2018-20024 A | 2/2018 |
| JP | 2018-23675 A | 2/2018 |
| JP | 2018-033717 A | 3/2018 |
| WO | 2017/030058 A1 | 2/2017 |
| WO | 2017218738 A1 | 12/2017 |

OTHER PUBLICATIONS

Japanese Office Action dated Aug. 9, 2022 in corresponding Japanese Patent Application No. 2018-113011 (with machine-generated English translation), 10 pages.

Extended European Search Report dated Feb. 9, 2022, in European Application No. 19819291.6.

Japanese Reasons for Refusal dated Mar. 2, 2022, in Japanese Application No. 2018-113011.

International Search Report and Written Opinion dated Jun. 25, 2019, received for PCT Application No. PCT/JP2019/016099, Filed on Apr. 15, 2019, 8 pages including English Translation.

OPHTHALMIC APPARATUS, METHOD OF CONTROLLING THE SAME, METHOD OF OPHTHALMIC OPTICAL COHERENCE TOMOGRAPHY, AND RECORDING MEDIUM

CROSS-REFERENCE TO RELATED APPLICATIONS

This application is a national stage (under 35 U.S.C. 371) of International Patent Application No. PCT/JP2019/016099, filed Apr. 15, 2019, claiming priority to Japanese Patent Application No. 2018-113011, filed Jun. 13, 2018, both of which are herein incorporated by reference in their entirety.

FIELD

The present invention relates to an ophthalmic apparatus, a method of controlling the same, a method of ophthalmic optical coherence tomography, a program, and a recording medium.

BACKGROUND

Various kinds of imaging apparatuses and measuring apparatuses are utilized in ophthalmic medical care. In recent years, ophthalmic apparatuses to which optical coherence tomography (OCT) technology is applied are widely used (see Japanese Unexamined Patent Application Publication No. 2018-023675, for example). OCT is typically applied to eye fundus imaging, anterior eye segment imaging, tissue thickness measurement, ocular axial length measurement, and the like.

In order to apply OCT to a living eye, various preparatory operations are required to be carried out in an accurate and appropriate manner. Such preparatory operations include the followings: position adjustment (alignment) of the optical system with respect to a target site; adjustment of the depiction position of the target site in the image frame; adjustment of image quality (signal to noise ratio), and the like. In addition, it is necessary to conduct imaging and/or measurement at an appropriate timing after checking whether or not these conditions have been satisfied.

A person skilled in handling ophthalmic apparatuses may be able to conduct such a series of preparatory operations accurately, appropriately and promptly by performing operations on the ophthalmic apparatus according to eye movements, and/or by sending instructions to the subject. However, in the cases where an ophthalmic apparatus is used in a situation in which no expert is present at that examination place, it may impose an excessive burden on the subject and the examiner.

SUMMARY

An object of the present invention is to reduce the burden on the subject and the examiner by automating a preparatory operation for applying OCT to a living eye, particularly the anterior segment thereof.

The first aspect of an embodiment example is an ophthalmic apparatus comprising: an optical coherence tomography (OCT) optical system configured to apply an OCT scan to an anterior segment of an eye; an image constructing unit configured to construct an image based on data acquired by the OCT scan; an artifact detecting unit configured to analyze the image constructed by the image constructing unit to detect an artifact along an A-scan direction; a movement mechanism configured to move the OCT optical system; a first movement controller configured to perform control of the movement mechanism based on the artifact detected by the artifact detecting unit; a corneal image detecting unit configured to analyze the image constructed by the image constructing unit to detect a corneal image; a position judging unit configured to judge whether an intersection of the artifact detected by the artifact detecting unit and the corneal image detected by the corneal image detecting unit is located within a predetermined area in an image frame; an image quality evaluating unit configured to calculate an image quality evaluation value of the image constructed by the image constructing unit; and a scan controller configured to perform control of the OCT optical system to apply an OCT scan of a predetermined pattern to the anterior segment, if the position judging unit judges that the intersection is located within the predetermined area and the image quality evaluation value calculated by the image quality evaluating unit is equal to or greater than a predetermined threshold.

The second aspect of the embodiment example is the ophthalmic apparatus of the first aspect, wherein after the first movement controller performs the control of the movement mechanism, the OCT optical system applies an OCT scan to the anterior segment, the image constructing unit constructs an image based on data acquired by the OCT scan, the artifact detecting unit analyzes the image to detect an artifact; the corneal image detecting unit analyzes the image to detect a corneal image, and the position judging unit judges whether an intersection of the artifact and the corneal image is located within a predetermined area in a frame of the image.

The third aspect of the embodiment example is the ophthalmic apparatus of the second aspect, wherein the image quality evaluating unit performs calculation of an image quality evaluation value after the position judging unit judges whether the intersection is located within the predetermined area.

The fourth aspect of the embodiment example is the ophthalmic apparatus of the second or third aspect, further comprising: an anterior segment photographing system configured to photograph the anterior segment; a destination determining unit configured to analyze an anterior segment image acquired by the anterior segment photographing system to determine a destination of the OCT optical system; and a second movement controller configured to perform control of the movement mechanism based on the destination determined by the destination determining unit, wherein the OCT optical system starts application of an OCT scan to the anterior segment after the second movement controller performs the control of the movement mechanism.

The fifth aspect of the embodiment example is the ophthalmic apparatus of the fourth aspect, wherein the destination determining unit sets the destination at a pupil center of the anterior segment, and the OCT optical system starts application of an OCT scan of a pattern with a scan center located at the pupil center.

The sixth aspect of the embodiment example is the ophthalmic apparatus of the fifth aspect, wherein the OCT optical system starts application of an iterative OCT scan of a pattern with a scan center located at the pupil center, and the image constructing unit constructs a plurality of images based respectively on a plurality of pieces of data sequentially acquired by the iterative OCT scan.

The seventh aspect of the embodiment example is the ophthalmic apparatus of the sixth aspect, wherein the iterative OCT scan includes an iterative B-scan.

The eighth aspect of the embodiment example is the ophthalmic apparatus of the sixth or seventh aspect, wherein the OCT optical system continues the iterative OCT scan at least until the image quality evaluating unit obtains an image quality evaluation value equal to or greater than the predetermined threshold.

The ninth aspect of the embodiment example is the ophthalmic apparatus of any of the first to eighth aspects, wherein the first movement controller performs the control of the movement mechanism to increase an intensity of an artifact detected by the artifact detecting unit.

The tenth aspect of the embodiment example is the ophthalmic apparatus of any of the first to ninth aspects, wherein the first movement controller performs the control of the movement mechanism such that an artifact detected by the artifact detecting unit passes through a center of an image frame.

The eleventh aspect of the embodiment example is the ophthalmic apparatus of any of the first to tenth aspects, wherein the image quality evaluating unit calculates, as the image quality evaluation value, a ratio between a signal of an anterior segment region and a noise of a background region in the image constructed by the image constructing unit.

The twelfth aspect of the embodiment example is the ophthalmic apparatus of the eleventh aspect, wherein the OCT optical system includes a measurement arm and a reference arm, the measurement arm being configured to guide measurement light to the anterior segment, and the reference arm being configured to guide reference light that is superposed on return light of the measurement light returning from the anterior segment, wherein at least one of the measurement arm and the reference arm includes a polarization device that changes a polarization state of light guided thereby, and the ophthalmic apparatus further comprising a polarization controller configured to perform control of the polarization device to increase the ratio calculated by the image quality evaluating unit.

The thirteenth aspect of the embodiment example is the ophthalmic apparatus of any of the first to twelfth aspects, further comprising a display controller configured to display the image constructed by the image constructing unit on a display device.

The fourteenth aspect of the embodiment example is the ophthalmic apparatus of the thirteenth aspect, wherein the display controller includes an artifact eliminating unit configured to eliminate the artifact detected by the artifact detecting unit from the image constructed by the image constructing unit, and displays on the display device an image obtained by eliminating the artifact by the artifact eliminating unit.

The fifteenth aspect of the embodiment example is a method of controlling an ophthalmic apparatus including an optical coherence tomography (OCT) optical system that applies an OCT scan to an anterior segment of an eye, an image constructing unit that constructs an image based on data acquired by the OCT scan, and a movement mechanism that moves the OCT optical system, the method comprising: an artifact detecting step of detecting an artifact along an A-scan direction by analyzing the image constructed by the image constructing unit; a movement control step of performing control of the movement mechanism based on the artifact detected; a corneal image detecting step of detecting a corneal image by analyzing the image constructed by the image constructing unit; a position judging step of judging whether an intersection of the artifact detected and the corneal image detected is located within a predetermined area in an image frame; an image quality evaluating step of calculating an image quality evaluation value of the image constructed by the image constructing unit; and a scan control step of performing control of the OCT optical system to apply an OCT scan of a predetermined pattern to the anterior segment, if the intersection is judged to be located within the predetermined area and the image quality evaluation value calculated is equal to or greater than a predetermined threshold.

The sixteenth aspect of the embodiment example is a program causing a computer to execute the method of the fifteenth aspect.

The seventeenth aspect of the embodiment example is a computer-readable non-transitory recording medium storing the program of the sixteenth aspect.

According to the embodiment example, a preparatory operation for applying OCT to an anterior segment of a living eye can be automated, and the burden on the subject and the examiner can be reduced.

DETAILED DESCRIPTION

Figure 1:
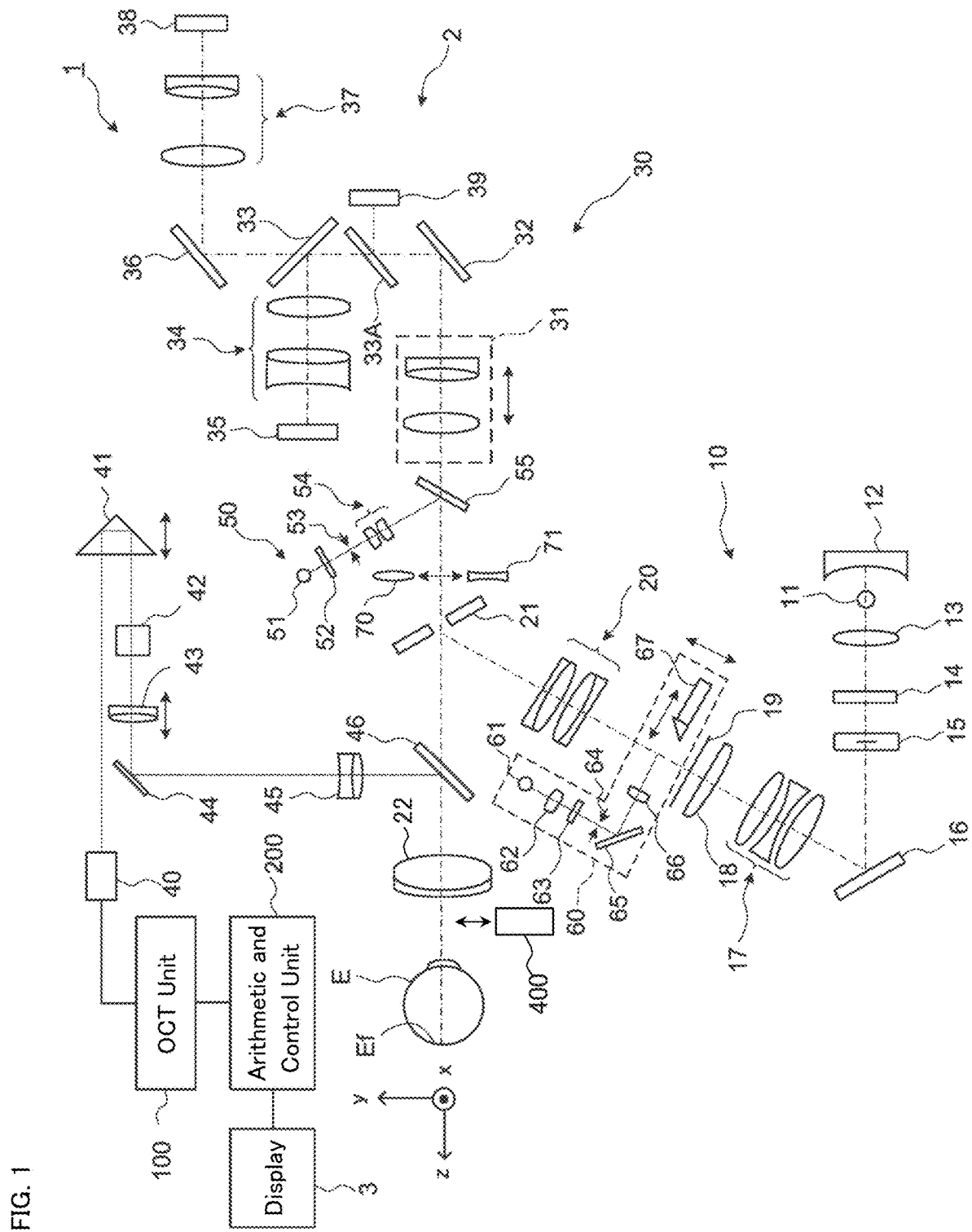
FIG. 1 is a schematic diagram illustrating an example of the configuration of the ophthalmic apparatus according to the embodiment example.

An ophthalmic apparatus, a method of controlling the same, a program, and a recording medium according to some embodiment examples and aspects thereof will be described in detail with referring to the drawings. The ophthalmic apparatus according to the embodiment examples is used to acquire data of a subject's eye in an optical manner (i.e., using light, in other words, using optical technology and technique). In particular, the ophthalmic apparatus according to the embodiment examples is capable of imaging the anterior eye segment using OCT techniques.

The ophthalmic apparatus according to the embodiment examples may have other functions in addition to the OCT function (optical coherence tomography apparatus). Examples of such additional functions include an anterior segment imaging function, a fundus imaging function, an ocular axial length measurement function, an ocular refractive power measurement function, an ocular aberration measurement function, a corneal shape measurement function, and a visual field measurement function. It should be noted that the additional functions are not limited to these examples and may be any kind of ophthalmic examination functions, or may be any examination functions usable in any medical departments other than ophthalmology.

While the following embodiment examples describe an ophthalmic apparatus (an ophthalmic imaging apparatus) of a combination of swept source OCT and a fundus camera, embodiment examples are not limited thereto. The type of OCT applicable to embodiment examples is not limited to swept source OCT, and may be spectral domain OCT, for example.

Swept source OCT is an imaging technique performed by: splitting light emitted from a wavelength tunable light source into measurement light and reference light; superposing return light of the measurement light returning from the object with the reference light to generate interference light; detecting the interference light by a photodetector such as a balanced photodiode; and applying Fourier transform and other processes to the detection data acquired according to the wavelength sweeping and the measurement light scanning.

Spectral domain OCT is an imaging technique performed by: splitting light from a low coherence light source into measurement light and reference light; superposing return light of the measurement light returning from the object with the reference light to generate interference light; detecting the spectral distribution of the interference light using a spectrometer; and applying Fourier transform and other processes to the spectral distribution detected.

As described above, swept source OCT is an OCT technique for acquiring a spectral distribution by time division, and spectral domain OCT is an OCT technique for acquiring a spectral distribution by space division. In addition, OCT techniques applicable to embodiment examples are not limited to these two, and may be any other morphological (structural) imaging OCT techniques such as time domain OCT or any functional imaging OCT techniques such as polarization OCT or blood flow measurement OCT.

In addition to such an ophthalmic apparatus, the following embodiment examples include descriptions of a method of controlling an ophthalmic apparatus, a program that causes an ophthalmic apparatus including a computer or a computer connected to an ophthalmic apparatus to execute such a control method, and a recording medium that stores such a program.

In the present disclosure, "image data" and an "image" displayed based thereon may not be distinguished from one another unless otherwise mentioned. Likewise, a site or tissue of the subject's eye and an image representing the site or the tissue may not be distinguished from one another unless otherwise mentioned.

<Configuration of Ophthalmic Apparatus>

FIG. 1 shows the exemplary ophthalmic apparatus 1. The ophthalmic apparatus 1 includes the fundus camera unit 2, the OCT unit 100, and the arithmetic and control unit 200. The fundus camera unit 2 includes optical systems and mechanisms for acquiring front images of the subject's eye E, and optical systems and mechanisms for performing an OCT scan. The OCT unit 100 includes optical systems and mechanisms for performing an OCT scan. The arithmetic and control unit 200 includes a storage, and one or more processors configured to execute various kinds of processes (e.g., calculations, operations, and controls).

The ophthalmic apparatus 1 includes a lens unit for switching sites of the subject's eye to which an OCT scan is applied. More specifically, the ophthalmic apparatus 1 of the present embodiment example includes the anterior segment OCT attachment 400 for applying an OCT scan to an anterior segment. For example, the anterior segment OCT attachment 400 may have the same configuration as that of the optical unit disclosed in Japanese Unexamined Patent Application Publication No. 2015-160103.

As shown in FIG. 1, the anterior segment OCT attachment 400 can be disposed between the objective lens 22 and the subject's eye E. When the anterior segment OCT attachment 400 is placed in the optical path, the ophthalmic apparatus 1 can apply an OCT scan to the anterior eye segment. On the other hand, when the anterior segment OCT attachment 400 is retracted from the optical path, the ophthalmic apparatus 1 can apply an OCT scan to the posterior eye segment. The insertion and removal of the anterior segment OCT attachment 400 is carried out manually or automatically.

Another embodiment example may be configured to apply an OCT scan to a posterior eye segment when an attachment is placed in the optical path, and apply an OCT scan to an anterior eye segment when the attachment is retracted from the optical path. Further, the sites switched by the attachment are not limited to the posterior eye segment and the anterior eye segment, and may be any sites of an eye. The configurations for switching the sites to which an OCT scan is applied are not limited to the attachments described above, and the following options may be adopted: a configuration including a lens movable along an optical path; or a configuration including a lens insertable into and removable from an optical path.

The "processor" as used in the present disclosure is hardware for executing a set of commands described in a software program. Such a processor typically includes an arithmetic unit, a resistor, a peripheral circuit, and the like. For example, the processor refers to a circuit or an electrical circuit configuration (or circuitry) such as a central processing unit (CPU), a graphics processing unit (GPU), a microprocessing unit (MPU), a digital signal processor (DSP), an application specific integrated circuit (ASIC), a programmable logic device (e.g., a simple programmable logic device (SPLD), a complex programmable logic device (CPLD), or a field programmable gate array (FPGA)), or the like. For example, the processor loads a program stored in storage hardware (e.g., a memory circuit or a storage), and executes the program, thereby implementing the functions according to a corresponding embodiment example. The processor may include at least part of the storage hardware.

<Fundus Camera Unit 2>

The fundus camera unit 2 is provided with optical systems for photographing the fundus Ef of the subject's eye E. Digital images of the fundus Ef (referred to as fundus images, fundus photographs, or the like) obtained by the fundus camera unit 2 are, in general, front images such as observation images and photographed images. An observation image is obtained by capturing a moving image using near-infrared light. A photographed image is a still image obtained by using flash light in the visible range.

The fundus camera unit 2 includes the illumination optical system 10 and the photography optical system 30. The illumination optical system 10 projects illumination light onto the subject's eye E. The photography optical system 30 detects the return light of the illumination light projected onto the subject's eye E. The measurement light incident from the OCT unit 100 is directed to the subject's eye E through the optical path in the fundus camera unit 2. The return light of the measurement light projected onto the subject's eye E (e.g., the fundus Ef) is directed to the OCT unit 100 through the same optical path in the fundus camera unit 2.

The light output from the observation light source 11 of the illumination optical system 10 (referred to as observation illumination light) is reflected by the concave mirror 12, passes through the condenser lens 13, and becomes near-infrared light after passing through the visible cut filter 14. Further, the observation illumination light is once converged at a location near the photographing light source 15, reflected by the mirror 16, passes through the relay lens system 17, the relay lens 18, the diaphragm 19, and the relay lens system 20, and is directed to the aperture mirror 21. Then, the observation illumination light is reflected on the peripheral part (i.e., the surrounding area of the aperture part) of the aperture mirror 21, penetrates the dichroic mirror 46, and is refracted by the objective lens 22, thereby illuminating the subject's eye E (the fundus Ef thereof). The return light of the observation illumination light from the subject's eye E is refracted by the objective lens 22, penetrates the dichroic mirror 46, passes through the aperture part formed in the center area of the aperture mirror 21, passes through the dichroic mirror 55, travels through the photography focusing lens 31, and is reflected by the mirror 32. Further, the return light passes through the half mirror 33A, is reflected by the dichroic mirror 33, and forms an image on the light receiving surface of the image sensor 35 by the imaging lens 34. The image sensor 35 detects the return light at a predetermined frame rate (capture rate). Note that the focus of the photography optical system 30 is adjusted to match the fundus Ef or the anterior segment.

The light output from the photographing light source 15 (referred to as photographing illumination light) passes through the same route as that of the observation illumination light and is projected onto the fundus Ef. The return light of the photographing illumination light from the subject's eye E passes through the same route as that of the return light of the observation illumination light, is guided to and passes through the dichroic mirror 33, is reflected by the mirror 36, and forms an image on the light receiving surface of the image sensor 38 by the imaging lens 37.

The liquid crystal display (LCD) 39 displays a fixation target (i.e., a fixation target image). Part of the light beam output from the LCD 39 is reflected by the half mirror 33A, reflected by the mirror 32, travels through the photography focusing lens 31 and the dichroic mirror 55, and passes through the aperture part of the aperture mirror 21. The light beam having passed through the aperture part of the aperture mirror 21 penetrates the dichroic mirror 46, and is refracted by the objective lens 22, thereby being projected onto the fundus Ef. Fixation targets are typically used for guidance and fixation of the line of sight. The direction in which the line of sight of the subject's eye E is guided (and fixed), that is, the direction in which the fixation of the subject's eye E is urged is referred to as a fixation position.

The fixation position can be changed by changing the display position of the fixation target image on the screen of the LCD 39. Examples of fixation positions include a fixation position for acquiring an image centered on the macula, a fixation position for acquiring an image centered on the optic nerve head, a fixation position for acquiring an image centered on a position between the macula and the optic nerve head (i.e., the fundus center position), and a fixation position for acquiring an image of a site far away from the macula (i.e., a peripheral position of the fundus).

A user interface such as a graphical user interface (GUI) for designating at least one of such typical fixation positions can be provided. Further, a user interface such as a GUI for manually changing the fixation position (i.e., the display position of the fixation target) can be provided. In addition, it is also possible to apply a configuration in which the fixation position is automatically set.

The configuration of presenting fixation targets to the subject's eye E for changing fixation positions is not limited to display devices such as LCD. For example, a device that has light emitting elements (e.g., light emitting diodes) disposed in a matrix-like arrangement (referred to as a fixation matrix) can be adopted in place of a display device. In this case, fixation positions of the subject's eye E by the fixation target can be changed by lighting one (or more) of the light emitting elements in a selective manner. As another example, a device provided with one or more movable light emitting elements can generate the fixation target capable of changing fixation positions.

The alignment optical system 50 generates an alignment indicator used for the alignment of the optical system with respect to the subject's eye E. The alignment light output from the light emitting diode (LED) 51 travels through the diaphragm 52, the diaphragm 53, and the relay lens 54, is reflected by the dichroic mirror 55, passes through the aperture part of the aperture mirror 21, penetrates the dichroic mirror 46, and is projected onto the subject's eye E via the objective lens 22. The return light of the alignment light from the subject's eye E passes through the same route as that of the return light of the observation illumination light and is guided to the image sensor 35. Based on the received image (referred to as the alignment indicator image), manual alignment and/or automatic alignment can be performed.

Alignment methods applicable to embodiment examples are not limited to the above method using an alignment indicator. For example, an alignment method may be applied using trigonometry and an anterior segment camera capable of photographing the anterior segment from two or more positions that are different from each other (see, for example, Japanese Unexamined Patent Application Publication No. 2013-248376 and Japanese Unexamined Patent Application Publication No. 2016-047094). This method is referred to as stereo alignment or the like. Alternatively, a method using an optical lever configured to project light onto the cornea from an oblique direction and detect the cornea reflection light in the opposite oblique direction can be applied (see, for example, Japanese Unexamined Patent Application Publication No. 2016-047094). Further, alignment may be performed by detecting a feature point (e.g., the center of the pupil) from an infrared observation image of the anterior segment. This method will be described later.

The focus optical system 60 generates a split indicator used for the focus adjustment with respect to subject's eye E. The focus optical system 60 is moved along the optical path of the illumination optical system 10 (referred to as the illumination optical path) in conjunction with the movement of the photography focusing lens 31 along the optical path of the photography optical system 30 (referred to as the photographing optical path). The reflection rod 67 is inserted into and removed from the illumination optical path. Before performing focus adjustment, the reflective surface of the reflection rod 67 is arranged in the slanted state in the illumination optical path. The focus light output from the LED 61 passes through the relay lens 62, is split into two light beams by the split indicator plate 63, passes through the two-hole diaphragm 64. Then, the focus light is reflected by the mirror 65, is converged on the reflective surface of the reflection rod 67 by the condenser lens 66, and is reflected by the reflective surface. Further, the focus light travels through the relay lens 20, is reflected by the aperture mirror 21, and penetrates the dichroic mirror 46, thereby being projected onto the subject's eye E via the objective lens 22. The return light of the focus light from the subject's eye E (e.g., the fundus reflection light) passes through the same route as that of the return light of the alignment light and is guided to the image sensor 35. Based on the received image (referred to as the split indicator image), manual focusing and/or automatic focusing can be performed.

The diopter correction lenses 70 and 71 can be selectively inserted into the photographing optical path between the aperture mirror 21 and the dichroic mirror 55. The diopter correction lens 70 is a positive lens (convex lens) for correcting high hyperopia. The diopter correction lens 71 is a negative lens (concave lens) for correcting high myopia.

The dichroic mirror 46 couples the optical path for photography and the optical path for OCT scanning (measurement arm). The dichroic mirror 46 reflects the light of wavelength bands used for OCT scanning and transmits the light of wavelength bands used for photography. The measurement arm is formed by, listed from the OCT unit 100 side, the collimator lens unit 40, the retroreflector 41, the dispersion compensation member 42, the OCT focusing lens 43, the optical scanner 44, and the relay lens 45.

The retroreflector 41 is movable along the optical path of the measurement light LS incident on the retroreflector 41, whereby the length of the measurement arm is changed. The change in the length of the measurement arm can be utilized for operations such as optical path length correction according to axial length and interference condition adjustment.

The dispersion compensation member 42 acts to eliminate the difference between the dispersion characteristics of the measurement light LS and that of the reference light LR, together with the dispersion compensation member 113 (described later) arranged in the reference arm.

The OCT focusing lens 43 is moved along the measurement arm in order to perform the focus adjustment of the measurement arm. Note that the movements of the photography focusing lens 31, the focus optical system 60, and the OCT focusing lens 43 may be controlled in an interlocking manner.

The optical scanner 44 is placed at a position substantially optically conjugate with respect to the pupil of the subject's eye E when the anterior segment OCT attachment 400 is removed from the optical path. On the other hand, the optical scanner 44 is placed at a position substantially optically conjugate with respect to the anterior segment of the subject's eye E (e.g., the cornea, the anterior chamber, the pupil, or the crystalline lens) when the anterior segment OCT attachment 400 is placed in the optical path. The optical scanner 44 is configured to deflect the measurement light LS guided through the measurement arm. An example of the optical scanner 44 is provided by a galvano scanner configured to be capable of two dimensional scanning. Typically, the optical scanner 44 includes a one dimensional scanner for deflecting the measurement light in the +x and −x directions (x-scanner), and another one dimensional scanner for deflecting the measurement light in the +y and −y directions (y-scanner). When such a configuration is employed, for example, either one of the x-scanner and the y-scanner may be placed at the optically conjugate position described above. Alternatively, the optically conjugate positions may be placed between the x-scanner and the y-scanner.

<OCT Unit 100>

Figure 2:
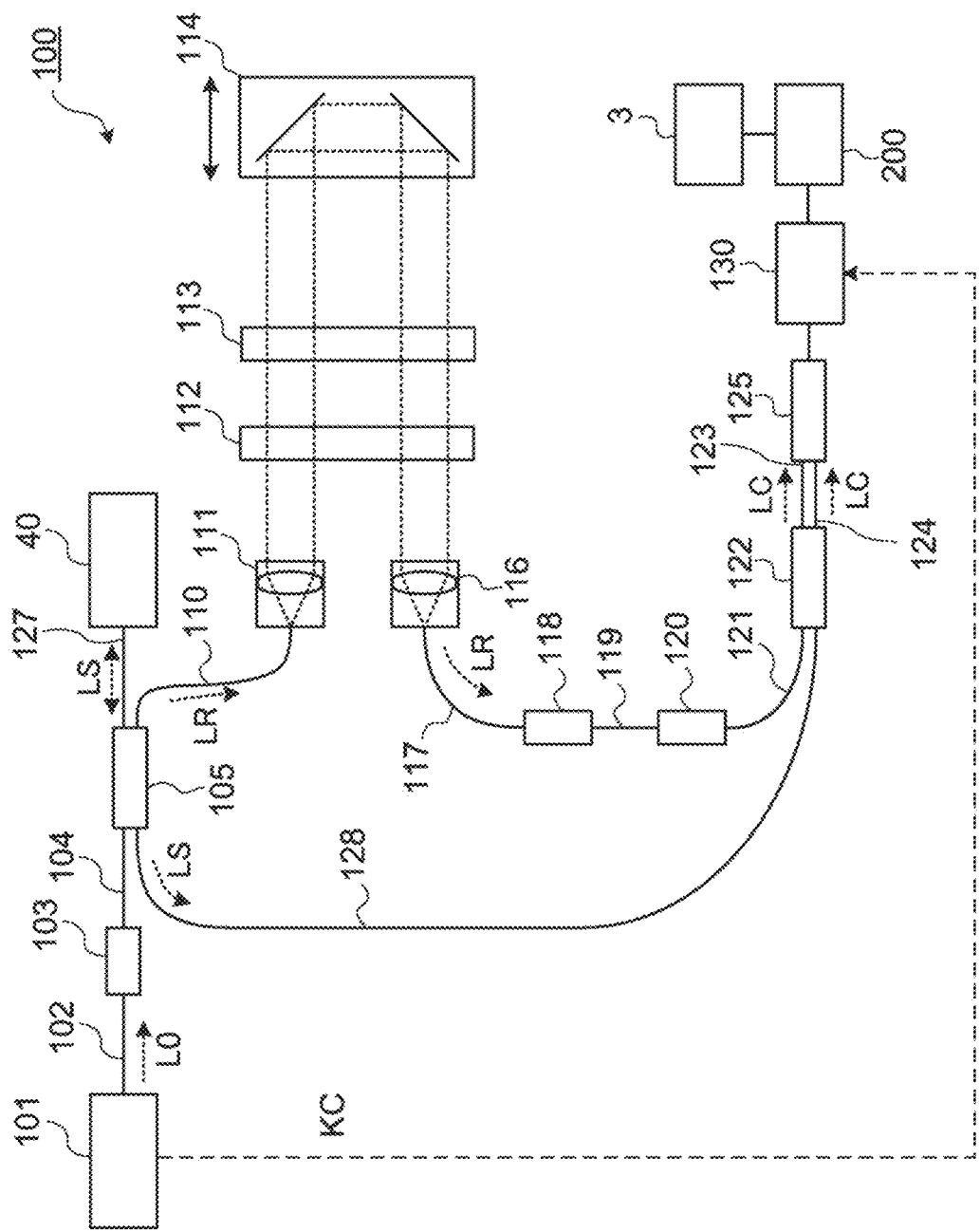
FIG. 2 is a schematic diagram illustrating an example of the configuration of the ophthalmic apparatus according to the embodiment example.

The exemplary OCT unit 100 shown in FIG. 2 is provided with the optical system for performing swept source OCT. The optical system includes an interference optical system. The interference optical system is configured to split light emitted from a wavelength tunable light source into measurement light and reference light, superpose the return light of the measurement light projected onto the subject's eye E with the reference light having traveled through the reference optical path, thereby yielding interference light. Then, the interference optical system detects the interference light. The data (i.e., a detection signal, an interference signal) obtained by detecting the interference light is a signal representing the spectrum of the interference light and is sent to the arithmetic and control unit 200.

The light source unit 101 includes, for example, a near-infrared wavelength tunable laser configured to vary wavelengths of emitted light at high speed. The low coherence light LO output from the light source unit 101 is guided to the polarization device 103 through the optical fiber 102, and the polarization state of the light LO is regulated. Further, the light LO with regulated polarization state is guided to the fiber coupler 105 through the optical fiber 104 and is split into the measurement light LS and the reference light LR. The optical path of the measurement light LS is referred to as a measurement arm, and the optical path of the reference light LR is referred to as a reference arm.

The reference light LR generated by the fiber coupler 105 is guided through the optical fiber 110 to the collimator 111, is converted into a parallel light beam, travels through the optical path length correction member 112 and the dispersion compensation member 113, and is guided to the retroreflector 114. The optical path length correction member 112 acts to match the optical path length of the reference light LR and that of the measurement light LS with each other. The dispersion compensation member 113 acts to eliminate the difference between the dispersion characteristics of the reference light LR and that of the measurement light LS with each other, together with the dispersion compensation member 42 arranged in the measurement arm. The retroreflector 114 is movable along the optical path of the reference light LR incident on the retroreflector 114. With this, the length of the reference arm is changed. The change in the length of the reference arm may be utilized for operations such as optical path length correction according to axial length and interference condition adjustment.

After passing through the retroreflector 114, the reference light LR travels through the dispersion compensation member 113 and the optical path length correction member 112, is converted from a parallel light beam to a convergent light beam by the collimator 116, and is incident on the optical fiber 117. The reference light LR having entered the optical fiber 117 is guided to the polarization device 118, and the polarization state of the reference light LR is regulated. Then, the reference light LR is guided to the attenuator 120 through the optical fiber 119, and the light amount of the reference light LR is regulated. Subsequently, the reference light LR is guided to the fiber coupler 122 through the optical fiber 121.

The polarization device 118 may be any type of polarization controlling device such as a bulk type, a paddle type, or an in-line type. A bulk type polarization controlling device is, typically, configured to change the polarization state with a series of optical element groups such as a half-wave plate, a quarter-wave plate, a lens, or the like. A paddle type polarization controlling device is, typically, configured to change the polarization state by utilizing birefringence induced by rotating a plurality of paddles, each of which forms an optical fiber into a coil-like shape. An in-line polarization controlling device is, typically, configured to change the polarization state by utilizing birefringence induced by applying an external force to an optical fiber or rotating an optical fiber. Likewise, the polarization device 103 may be any type of polarization controlling device.

Meanwhile, the measurement light LS generated by the fiber coupler 105 is guided to the collimator lens unit 40 through the optical fiber 127 and is converted to a parallel light beam. Then, the measurement light LS passes through the retroreflector 41, the dispersion compensation member 42, the OCT focusing lens 43, the optical scanner 44, and the relay lens 45, and then reaches the dichroic mirror 46. The measurement light LS is reflected by the dichroic mirror 46, is refracted by the objective lens 22, and is projected onto the subject's eye E. The measurement light LS is reflected and scattered at various depths of the subject's eye E. The return light of the measurement light LS returning from the subject's eye E travels along the measurement arm in the opposite direction to the measurement light LS traveling toward the subject's eye E, is directed to the fiber coupler 105, and then reaches the fiber coupler 122 via the optical fiber 128.

The fiber coupler 122 superposes the measurement light LS incident through the optical fiber 128 with the reference light LR incident through the optical fiber 121, to generate interference light. The fiber coupler 122 splits the generated interference light at a predetermined splitting ratio (e.g., 1 to 1) to generate a pair of interference light LC. The pair of interference light LC is guided to the detector 125 through the optical fibers 123 and 124, respectively.

The detector 125 includes, for example, a balanced photo diode. The balanced photodiode includes a pair of photodetectors for respectively detecting the pair of the interference light LC. The balanced photodiode outputs a difference between a pair of detection signals corresponding to the pair of the interference light LC respectively obtained by the pair of photodetectors. The detector 125 sends the output (difference signal) to the data acquisition system (DAQ) 130.

The clock KC is supplied from the light source unit 101 to the data acquisition system 130. The clock KC is generated in the light source unit 101 in synchronization with the output timings of wavelengths varied over a predetermined wavelength range by the wavelength tunable type light source. For example, the light source unit 101 is configured to split the light LO of each output wavelength to generate two pieces of split light, apply an optical delay to one of the two pieces of split light, combine the resulting two pieces of split light, detect the combined light, and generate the clock KC based on the detection signal of the combined light. The data acquisition system 130 performs sampling of the signal (difference signal) input from the detector 125 based on the clock KC. The data acquisition system 130 sends the data obtained by the sampling to the arithmetic and control unit 200.

While both an element for changing the measurement arm length (e.g., the retroreflector 41) and an element for changing the reference arm length (e.g., the retroreflector 114 or a reference mirror) are provided in the present embodiment example, only one of these two elements may be provided in some other embodiment examples. Further, elements for changing the difference between the measurement arm length and the reference arm length (i.e., optical path length difference) are not limited to the elements in the present embodiment example, and any type of element (e.g., any type of optical member, any type of mechanism) may be employed.

<Arithmetic and Control Unit 200>

The arithmetic and control unit 200 controls each part (each element) of the ophthalmic apparatus 1. Further, the arithmetic and control unit 200 executes various kinds of arithmetic processes. For example, the arithmetic and control unit 200 applies signal processing such as Fourier transform on the spectral distribution based on a sampling data group collected by the data acquisition system 130 for each series of wavelength scanning (for each A-line), to create reflection intensity profiles respectively for A-lines. Furthermore, the arithmetic and control unit 200 applies imaging processing to the reflection intensity profiles for the A-lines to construct image data. Arithmetic processes for the image data construction are the same as those of conventional swept source OCT.

The arithmetic and control unit 200 includes, for example, a processor, random access memory (RAM), read only memory (ROM), hard disk drive, and communication interface. A storage such the hard disk drive stores various kinds of computer programs. The computer programs are executed by the processor of the arithmetic and control unit 200. The arithmetic and control unit 200 may include an operation device, an input device, a display device, etc.

<User Interface 240>

The user interface 240 includes the display device 241 and the operation device 242. The display device 241 includes the display 3. The operation device 242 includes various kinds of operation devices and input devices. The user interface 240 may include a device having both the display function and the operation function, such as a touch panel display. Some embodiment examples may be configured not to include at least part of the user interface 240. For example, the display device may be a peripheral device connected to the ophthalmic apparatus. Further, at least part of the operation device and/or at least a part of the input device may be a peripheral device connected to the ophthalmic apparatus.

<Processing System>

Figure 3A:
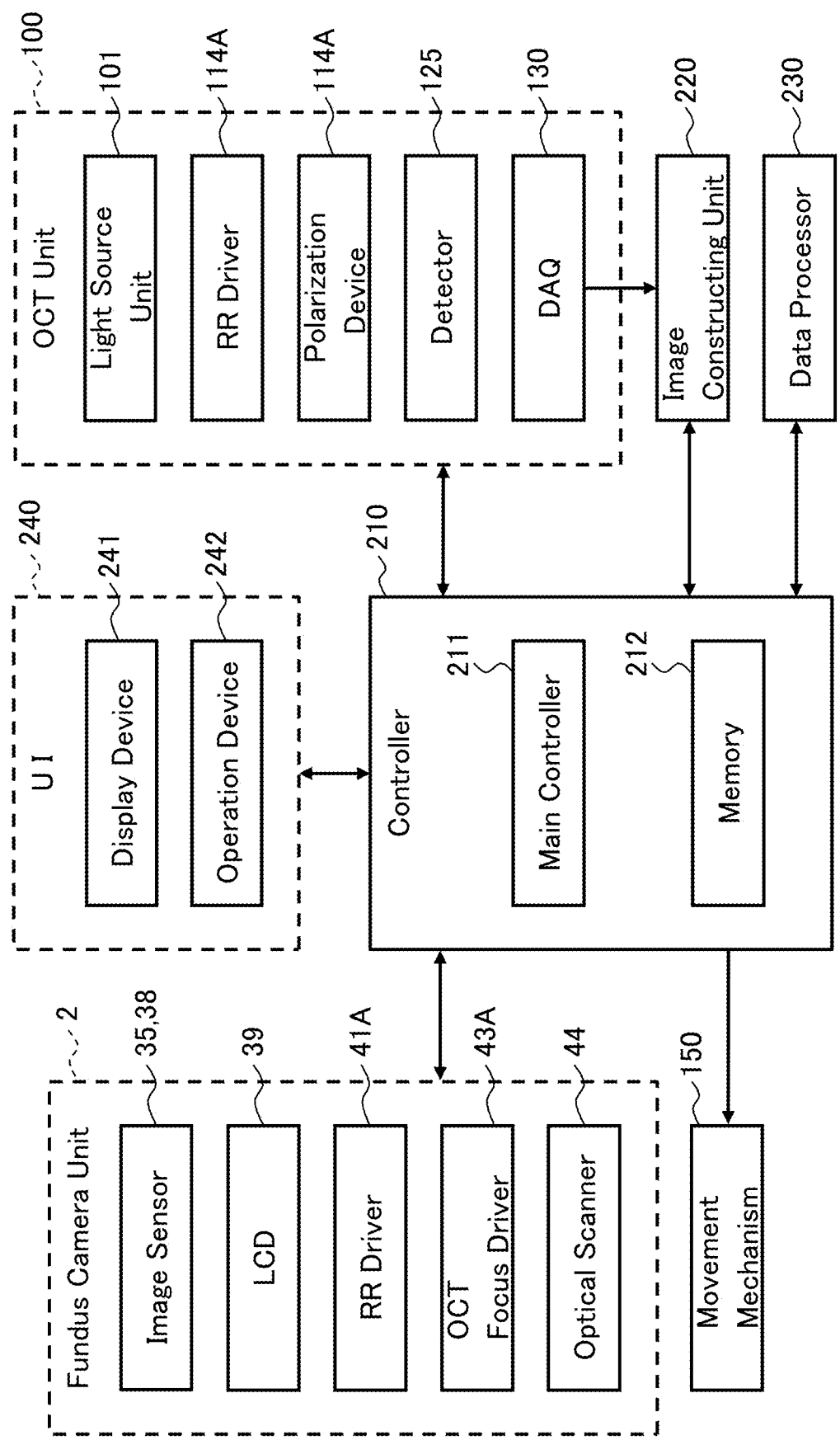
FIG. 3A is a schematic diagram illustrating an example of the configuration of the ophthalmic apparatus according to the embodiment example.
Figure 3B:
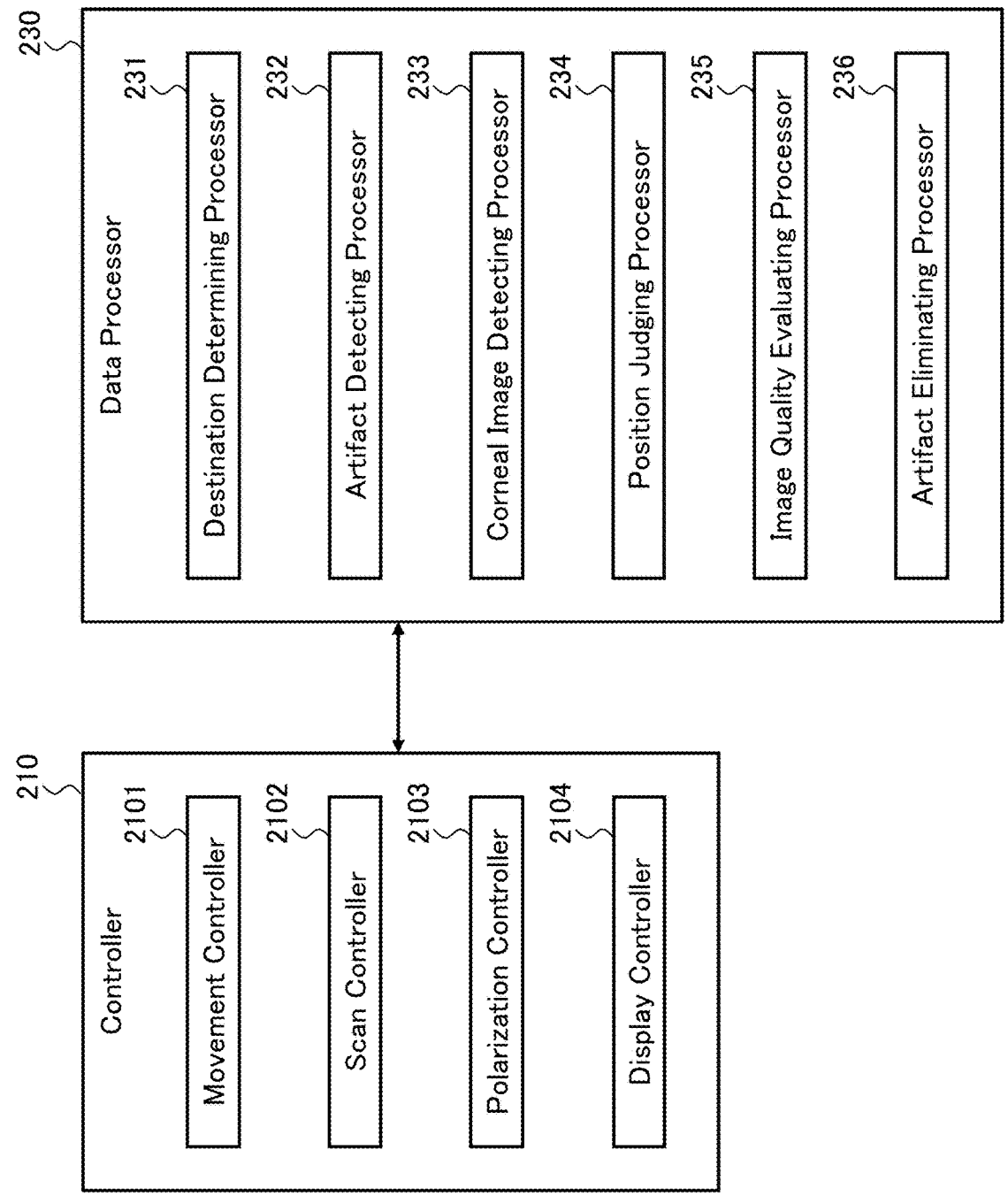
FIG. 3B is a schematic diagram illustrating an example of the configuration of the ophthalmic apparatus according to the embodiment example.

FIG. 3A and FIG. 3B show an exemplary configuration of the processing system of the ophthalmic apparatus 1. The controller 210, the image constructing unit 220, and the data processor 230 may be provided in the arithmetic and control unit 200, for example.

<Controller 210>

The controller 210 includes a processor and controls each part (each element) of the ophthalmic apparatus 1. The controller 210 includes the main controller 211 and the memory 212.

<Main Controller 211>

The main controller 211 controls each element of the ophthalmic apparatus 1 (including the elements shown in FIG. 1 to FIG. 3B). The function of the main controller 211 may typically be implemented by the cooperation of hardware including a processor and software including a control program. At least part of the functions of the main controller 211 may be implemented by means of hardware including a control circuit.

The photography focusing lens 31 disposed in the photography optical path and the focus optical system 60 disposed in the illumination optical path are moved in an integral or interlocking manner by a photography focus driver (not shown in the drawings) under control of the main controller 211. The retroreflector 41 disposed in the measurement arm is moved by the retroreflector driver (RR driver) 41A under control of the main controller 211. The OCT focusing lens 43 disposed in the measurement arm is moved by the OCT focus driver 43A under control of the main controller 211. The optical scanner 44 provided in the measurement arm operates under control of the main controller 211. The retroreflector 114 disposed in the reference arm is moved by the retroreflector driver (RR driver) 114A under control of the main controller 211. The polarization device 118 disposed in the reference arm operates under control of the main controller 211. Similarly, the polarization device 103 disposed in the optical path of the light LO operates under control of the main controller 211. Each of the mechanisms described as examples here typically includes an actuator that operates under control of the main controller 211. The same applies to any mechanisms and any elements not described here.

The movement mechanism 150 is configured to move, for example, the fundus camera unit 2 in a three dimensional manner. In a typical example, the movement mechanism 150 includes the followings: an x-stage movable in the +x and −x directions (i.e., left and right directions); an x-movement mechanism that moves the x-stage; a y-stage movable in the +y and −y directions (i.e., up and down directions); a y-movement mechanism that moves the y-stage; a z-stage movable in the +z and −z directions (i.e., depth direction); and a z-movement mechanism that moves the z-stage. Each of the movement mechanisms described here includes an actuator such as a pulse motor that operates under control of the main controller 211. At least part of the measurement arm (including at least the objective lens 22) is directly or indirectly placed on the stages. Typically, the fundus camera unit is placed directly or indirectly on the stages.

<Memory 212>

The memory 212 stores various kinds of data. Examples of the data stored in the memory 212 include OCT image data, anterior segment image data, fundus image data, and subject's eye information. The subject's eye information may include subject information such as patient identifiers and patient's names, identifiers for the left eye and the right eye, and electronic medical record data, for example. Further, the memory 212 may store various kinds of templates, various kinds of parameter values, and various kinds of software for operating the ophthalmic apparatus 1.

The memory 212 typically includes a storage having a relatively large capacity such as a hard disk. Note that various kinds of data may be stored in a storage or an information processing apparatus on a communication line. If this is the case, the memory 212 does not need to include the storage having a relatively large capacity. The same applies if a relatively large capacity storage is employed as a peripheral device of the ophthalmic apparatus 1.

<Image Constructing Unit 220>

The image constructing unit 220 constructs OCT image data based on data acquired by the data acquisition system 130. The function of the image constructing unit 220 may typically be implemented by the cooperation of hardware including a processor and software including an image constructing program. At least part of the function of the image constructing unit 220 may be implemented by hardware including an image constructing circuit.

The image constructing unit 220 constructs cross sectional image data based on data acquired by the data acquisition system 130. The image construction processing includes signal processing such as noise elimination (noise reduction), filtering, fast Fourier transform (FFT), and other processes as in conventional swept source OCT.

Image data constructed by the image constructing unit 220 is a data set including a group of a plurality of pieces of image data constructed by applying imaging processing to reflection intensity profiles at corresponding A-lines arranged in the area to which an OCT scan is applied. Each of the A-lines is a scan line lying along the z direction.

An OCT scan applied to an A-line is referred to as an A-scan. Image data obtained by an A-scan may be called A-scan image data. Further, the z direction may be referred to as the A-scan direction.

A collection of a plurality of A-scans arranged in a one dimensional direction (arbitrary direction in the xy-plane) orthogonal to the A-scan direction is referred to as a B-scan. The one dimensional direction orthogonal to the A-scan direction may be referred to as the B-scan direction. Image data obtained by a B-scan may be referred to as B-scan image data.

Image data constructed by the image constructing unit 220 is, for example, one or more pieces of A-scan image data, one or more pieces of B-scan image data, or three dimensional image data. Three dimensional image data is image data represented by a three dimensional coordinate system, and typical examples thereof include stack data and volume data. Stack data is constructed by embedding a plurality of pieces of B-scan image data in a single three dimensional coordinate system. Volume data, also referred to as voxel data, is constructed by applying voxelization processing to stack data.

The image constructing unit 220 may be configured to apply image processing to image data using any known image processing technique. For example, the image constructing unit 220 may construct new image data by applying rendering to three dimensional image data. Examples of the rendering method include volume rendering, maximum intensity projection (MIP), minimum intensity projection (MinIP), surface rendering, and multi planar reconstruction (MPR). Further, the image constructing unit 220 may be configured to construct projection data by projecting three dimensional image data in the z direction (i.e., the A-line direction, the depth direction). In addition, the image constructing unit 220 may be configured to construct a shadowgram by projecting part of three dimensional image data in the z direction. Here, the part of the three dimensional image data projected for the shadowgram construction is extracted by using segmentation, for example.

<Data Processor 230>

The data processor 230 performs various kinds of data processing. For example, the data processor 230 may be configured to apply image processing and/or analysis processing to OCT image data, and/or, apply image processing and/or analysis processing to observation image data or photographed image data. The function of the data processor 230 may typically be implemented by the cooperation of hardware including a processor and software including a data processing program. At least part of the function of the data processor 230 may be implemented by hardware including a data processing circuit.

<Details of Configuration Example of Processing System>

FIG. 3B shows an example of the configurations of the controller 210 and the data processor 230.

<Example of the Controller 210>

The controller 210 illustrated in FIG. 3B includes the movement controller 2101, the scan controller 2102, the polarization controller 2103, and the display controller 2104.

The movement controller 2101 executes control of the movement mechanism 150. The scan controller 2102 executes control of elements for performing the OCT scan, such as the light source unit 101 and the optical scanner 44. The polarization controller 2103 executes control of the polarization device 118. Further, the polarization controller 2103 may be configured to execute control of the polarization device 103 in addition to or instead of the control of the polarization device 118. The display controller 2104 executes control of the user interface 240 (the display device 241).

The function of the movement controller 2101, the function of the scan controller 2102, the function of the polarization controller 2103, and the function of the display controller 2104 each may typically be implemented by the cooperation of hardware including a processor and software including a control program. At least part of the functions of any of the movement controller 2101, the scan controller 2102, the polarization controller 2103, and the display controller 2104 may be implemented by hardware including a control circuit.

The main controller 211 includes the movement controller 2101, the scan controller 2102, the polarization controller 2103, and the display controller 2104. Any of the movement controller 2101, the scan controller 2102, the polarization controller 2103, and the display controller 2104 may include storage hardware (i.e., the memory 212). Processing executed by the movement controller 2101, processing executed by the scan controller 2102, processing executed by the polarization controller 2103, and processing executed by the display controller 2104 will be described later.

<Example of the Data Processor 230>

The data processor 230 illustrated in FIG. 3B includes the destination determining processor 231, the artifact detecting processor 232, the corneal image detecting processor 233, the position judging processor 234, the image quality evaluating processor 235, and the artifact eliminating processor 236.

The function of the destination determining processor 231, the function of the artifact detecting processor 232, the function of the corneal image detecting processor 233, the function of the position judging processor 234, the function of the image quality evaluating processor 235, and the function of the artifact eliminating processor 236 each may typically be implemented by the cooperation of hardware including a processor and software including a data processing program. At least part of the functions of any of the destination determining processor 231, the artifact detecting processor 232, the corneal image detecting processor 233, the position judging processor 234, the image quality evaluating processor 235, and the artifact eliminating processor 236 may be implemented by hardware including a data processing circuit. Any of the destination determining processor 231, the artifact detecting processor 232, the corneal image detecting processor 233, the position judging processor 234, the image quality evaluating processor 235, and the artifact eliminating processor 236 may include storage hardware.

The followings are descriptions of each of the elements included in the data processor 230.

<Destination Determining Processor 231>

The ophthalmic apparatus 1 of the present embodiment example is capable of performing anterior eye segment imaging using the fundus camera unit 2. For example, the ophthalmic apparatus 1 is capable of capturing an infrared moving image of the anterior segment of an eye using the observation illumination light and the image sensor 35.

The destination determining processor 231 analyzes an anterior segment image acquired by the fundus camera unit 2 to determine a destination (goal of movement) of an OCT optical system. The movement controller 2101 controls the movement mechanism 150 based on the destination determined by the destination determining processor 231.

The destination in the present embodiment example may be, for example, coordinates (x, y, z) representing a position of the fundus camera unit 2 moved by the movement mechanism 150, or a control parameter of the movement mechanism 150. As an example of the latter, if the actuator of the movement mechanism 150 is a pulse motor, the control parameter may include the number of pulses supplied to the pulse motor.

The types (kinds) of information determined as a destination by the destination determining processor 231 are not limited to the above examples. The type (kind) of information representing a destination is determined in advance, for example, according to the configuration of hardware such as a movement mechanism and/or the configuration of software for movement control.

The OCT optical system is an optical system for applying an OCT scan to the subject's eye E (and movement mechanisms and drive mechanisms for operating elements of the OCT optical system). The OCT optical system of the present embodiment example includes at least a series (set) of elements composing the measurement arm in the fundus camera unit 2. Specifically, the series of elements includes the collimator lens unit 40, the retroreflector 41, the dispersion compensation member 42, the OCT focusing lens 43, the optical scanner 44, the relay lens 45, the dichroic mirror 46, and the objective lens 22. The present embodiment example is configured to move, by the movement mechanism 150, the fundus camera unit 2 including the OCT optical system thus configured.

A description will be given of a typical example of destination determination. The ophthalmic apparatus 1 performs infrared moving image photography of the anterior segment of the subject's eye E using the fundus camera unit 2. In parallel with the infrared moving image photography, the destination determining processor 231 sequentially analyzes a plurality of anterior segment images (a frame group (group of frames) of a moving image) acquired by the fundus camera unit 2 in a successive manner, thereby acquiring time series data of destinations of the OCT optical system.

The time series destination data reflects eye movement of the subject's eye E and changes in the relative position between the subject's eye E and the fundus camera unit 2. Further, changes in the pupil diameter may affect the time series destination data.

Note that it is not necessary for the destination determining processor 231 to analyze all the anterior segment images acquired by the fundus camera unit 2. For example, the number of anterior segment images to be analyzed by the destination determining processor 231 may be reduced by applying a thinning process or a selection process.

A plurality of destinations acquired by the destination determining processor 231 in parallel with the infrared moving image photography of the anterior segment is sequentially sent to the movement controller 2101. The movement controller 2101 executes control of the movement mechanism 150 based on the destinations sequentially input from the destination determining processor 231. The control of the movement mechanism 150 is carried out as real time processing.

Such an exemplary process allows the fundus camera unit 2 to be moved in accordance with the time series change in the destinations represented by the time series destination data. As a result of this, the position of the OCT optical system can be automatically regulated according to eye movement of the subject's eye E (tracking).

The OCT optical system may start application of an OCT scan to the anterior segment of the subject's eye E at an arbitrary timing after the control of the movement mechanism 150 performed by the movement controller 2101. A specific example of the OCT scan application timing will be described later.

Figure 4A:
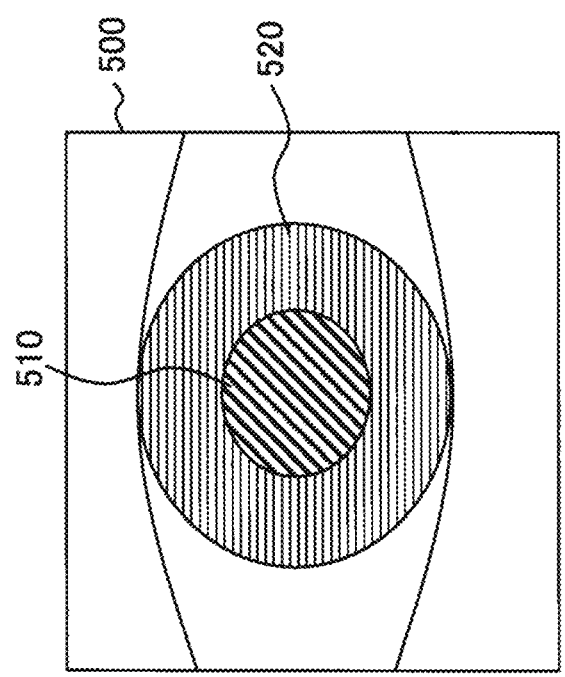
FIG. 4A is a schematic diagram for describing an operation that can be performed by the ophthalmic apparatus according to the embodiment example.

An example will be described of the destination determination processing performed by the destination determining processor 231. FIG. 4A shows an example of an anterior segment image acquired by the fundus camera unit 2. The anterior segment image 500 contains the pupil image 510 corresponding to the pupil of the subject's eye E and the iris image 520 corresponding to the iris. Here, the pupil image 510 is shown as an image region indicated by diagonal lines, and the iris image 520 is shown as an image region indicated by horizontal lines.

The destination determining processor 231 identifies at least one of the pupil image 510 and the iris image 520 by analyzing the anterior segment image 500. The analysis may include, for example, pixel-value-based thresholding and/or pattern detection.

A description will be given of a specific example of the thresholding. Since the pixel values of an anterior segment image of the present embodiment example are represented by the brightness gradation, the destination determining processor 231 can detect the pupil image 510 by identifying pixels whose brightness values are smaller than a first threshold determined in advance. The detection of the iris image 520 may employ a second threshold predetermined to be larger than the first threshold. Note that at least one of the first threshold and the second threshold may be a default value, or a relative value determined according to an arbitrary attribute and/or an arbitrary condition such as an anterior segment image subjected to be processed. As an example, the relative value may be a threshold determined on the basis of the brightness distribution, such as a brightness histogram, of an anterior segment image.

A description will be given of a specific example of the pattern detection. Utilizing the fact that the shape of the contour (outer edge, edge) of the pupil is substantially circular or substantially elliptical, the destination determining processor 231 may detect the pupil image 510 by identifying a region whose edge is of a substantially circular shape or a substantially elliptical shape. The same applies to the detection of the iris image 520. In the case of detecting both the pupil image 510 and the iris image 520, the destination determining processor 231 may be configured to first detect two substantially circular or substantially elliptical edges that are arranged substantially concentrically, and then set the image region whose outer edge is the inner one of the two detected edges as the pupil image 510, and set an image region of substantially annular shape surrounded by the inner edge and the outer edge as the iris image 520.

Note that techniques applicable to the analysis of anterior segment images are not limited to the above examples. For example, the anterior segment image analysis may include arbitrary image processing such as edge detection or binarization, and/or, may include arbitrary artificial intelligence techniques and/or arbitrary cognitive computing techniques.

Figure 4B:
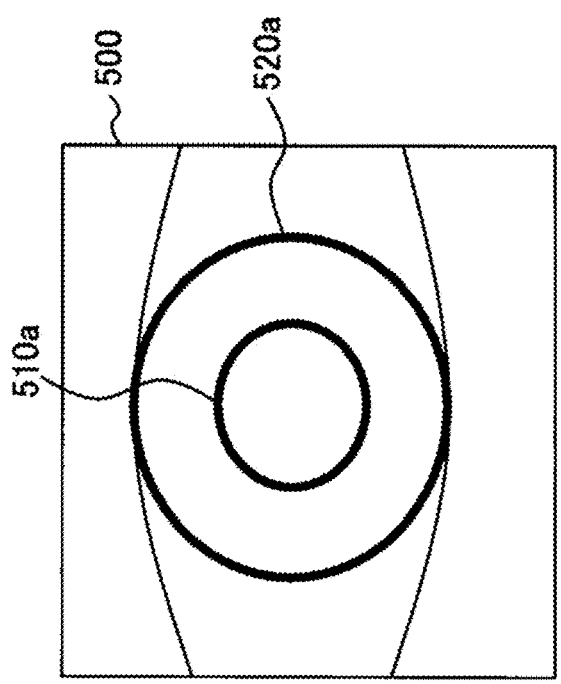
FIG. 4B is a schematic diagram for describing an operation that can be performed by the ophthalmic apparatus according to the embodiment example.

The reference character "510*a*" in FIG. 4B denotes the outer edge of the pupil image 510, and the reference character "520*a*" denotes the outer edge of the iris image 520. Here, at least one of the pupil outer edge 510*a* and the iris outer edge 520*a* may be an approximate circle or an approximate ellipse.

The destination determining processor 231 identifies the pupil center of the anterior segment based on at least one of the pupil image 510 and the iris image 520, for example, based on at least one of the pupil outer edge 510*a* and the iris outer edge 520*a*. The pupil center identification process may include at least one of the following processes, for example: a process of determining the center or the center of gravity of the pupil image 510; a process of determining the center or the center of gravity of the pupil outer edge 510*a*; a process of determining the center or the center of gravity of the iris image 520; and a process of determining the center or the center of gravity of the iris outer edge 520*a*. In the case where the pupil center identification process includes two or more of the four example processes, a statistical process (e.g., averaging) may be performed on two or more pupil center candidates respectively obtained by the two or more processes. Note that usable processes for pupil center determination is not limited to the above examples.

In the way described above, the destination determining processor 231 can detect the pupil center of the anterior segment of the subject's eye E and set the detected pupil center as a destination. The scan controller 2102 may set an area to which an OCT scan is applied such that the area passes through the pupil center detected.

The pattern of the OCT scan may be set in an arbitrary manner. For example, a line scan (B-scan), a cross scan, a multi-cross scan, a radial scan, or a three dimensional scan may be employed as the OCT scan pattern. The orientation of a line scan is optional. A cross scan is composed of two line scans orthogonal to each other. A multi-cross scan is composed of two line scan groups orthogonal to each other. Here, two or more line scans included in each of the line scan groups are parallel to one another. A radial scan is composed of a plurality of line scans arranged at equal angular intervals. A three dimensional scan is also referred to as a volume scan, and is typically a raster scan in which a large number of line scans are arranged in parallel to one another.

Figure 4C:
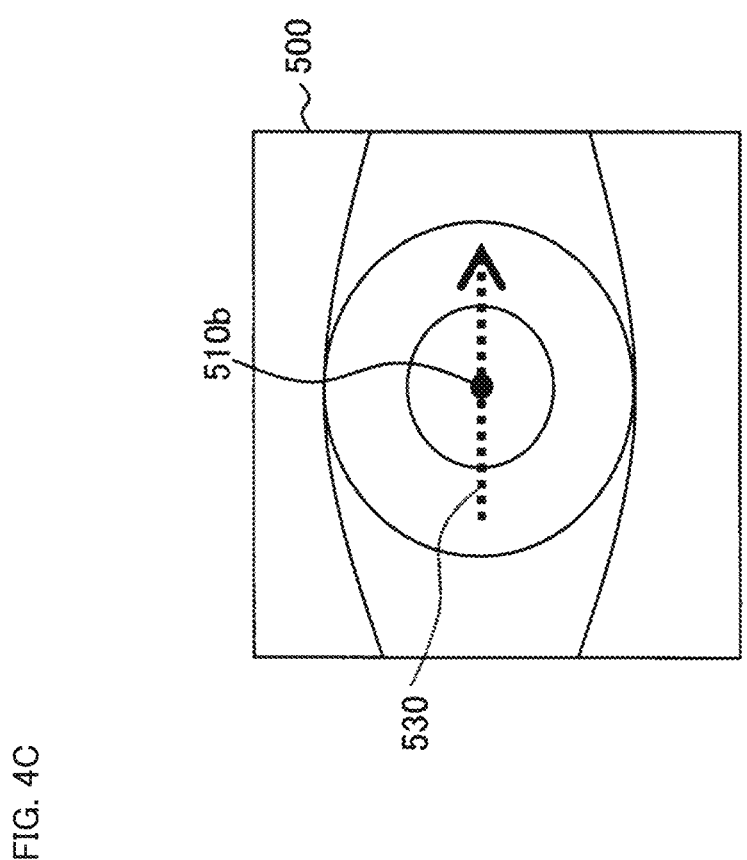
FIG. 4C is a schematic diagram for describing an operation that can be performed by the ophthalmic apparatus according to the embodiment example.

The scan controller 2102 may set an area to which an OCT scan is applied so that the center of the area is located at the pupil center detected by the destination determining processor 231. An example is given in FIG. 4C of the case where a line scan is employed. As shown in FIG. 4C, the scan controller 2102 may set an area to which the line scan 530 is applied such that the center of the line scan 530 and the pupil center 510*b* coincide with each other. Similarly, in the case where another scan pattern is employed, the scan controller 2102 may set an area to which an OCT scan is applied such that the center of a scan and the pupil center 510*b* coincide with each other.

The processing described above allows an OCT scan to be executed to pass substantially through the pupil center. The relative deviation between the xy-coordinates of the pupil center and the xy-coordinates of the corneal apex is not large in standard eyes. Therefore, the corneal apex or the vicinity thereof can be scanned if an OCT scan is performed with the pupil center as a scan target like the present embodiment example.

While the destination is set by detecting a feature point from an infrared observation image of the anterior segment in the present embodiment example, other methods may also be employed. For example, any other technique or method such as an alignment indicator, a stereo alignment, or an optical lever may be used to detect a feature point of the anterior segment. In the case of employing a technique or method capable of detecting the pupil center, the destination may be set to the pupil center detected. In the case of employing a technique or method capable of detecting the corneal apex, the destination may be set to the corneal apex detected. It should be noted that the feature point is not limited to the pupil center and the corneal apex.

<Artifact Detecting Processor 232>

The artifact detecting processor 232 analyzes the OCT image constructed by the image constructing unit 220 to detect an artifact along the A-scan direction.

Figure 5:
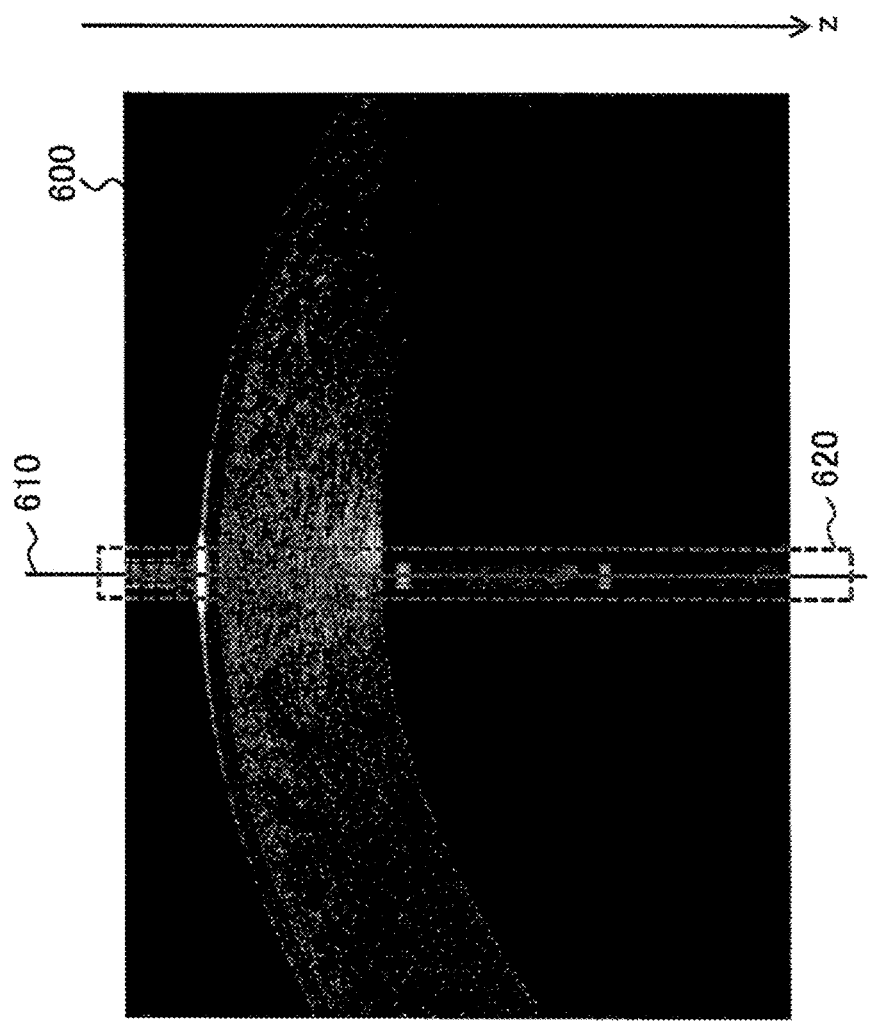
FIG. 5 is a schematic diagram for describing an operation that can be performed by the ophthalmic apparatus according to the embodiment example.

FIG. 5 shows an OCT image actually obtained using a B-scan (line scan) passing through the corneal apex. In the B-scan image 600, a high brightness image region with a shape similar to part of an annulus represents a corneal cross section. The shape of the upper edge of the corneal cross sectional image is a substantially circular arc shape that is convex upward, and the uppermost part thereof corresponds to the corneal apex. Note that the downward direction on FIG. 5 is the z-direction, that is, the A-scan direction. The reference character "610" denotes an A-line passing through the corneal apex. A band shaped or linear shaped artifact appears along the A-scan direction in the area 620 near the A-line. The occurrence of the artifact is attributable to reflection at the corneal apex and other factors. Such an artifact will be referred to as a longitudinal artifact.

The artifact detecting processor 232 may detect a longitudinal artifact based on a predetermined feature (characteristic) such as brightness, a position, or a shape. When brightness is taken into consideration, the artifact detecting processor 232 may detect an image region having brightness higher than a predetermined threshold as (a candidate of) a longitudinal artifact. When a position is taken into consideration, the artifact detecting processor 232 may detect the uppermost part of the upper edge of the corneal cross sectional image as the corneal apex and detect (a candidate of) a longitudinal artifact based on the position of the corneal apex detected. When a shape is taken into consideration, the artifact detecting processor 232 may detect a band shaped or linear shaped image region along the A-scan direction as (a candidate of) a longitudinal artifact.

The fact that the corneal apex has the highest brightness (see FIG. 5) may be utilized for detecting a longitudinal artifact. Any known segmentation technique may also be used to detect a longitudinal artifact. The technique or method for detecting a longitudinal artifact is not limited to the above examples. The corneal image detecting processor 233 may be configured to perform detection of a corneal image (e.g., corneal cross sectional image), or detection of part of a corneal image (e.g., corneal apex, edge).

The movement controller 2101 may perform control of the movement mechanism 150 based on the result of the longitudinal artifact detection performed by the artifact detecting processor 232. In other words, movement control of the OCT optical system may be performed by referring to a longitudinal artifact that occurs in an OCT image.

As a first example, the movement controller 2101 may be configured to execute control of the movement mechanism 150 so that the intensity of the longitudinal artifact occurring in the OCT image is maximized. The control performed by the present example may be implemented by iteratively performing a series of processes including OCT image acquisition, longitudinal artifact detection, and movement of the OCT optical system.

As a specific example thereof, the series of processes as follows may be executed while iteratively applying OCT scans of a predetermined pattern to the anterior segment to acquire time series OCT images. The artifact detecting processor 232 detects longitudinal artifacts in the OCT images sequentially acquired by the iterative OCT scan application. The movement controller 2101 (or, another element of the controller 210, another element of the artifact detecting processor 232, or another element of the data processor 230; the same applies below) determines the intensities of the longitudinal artifacts detected. The movement controller 2101 controls the movement mechanism 150 to move the OCT optical system.

Further, the artifact detecting processor 232 detects a longitudinal artifact in an OCT image acquired after the movement of the OCT optical system. The movement controller 2101 determines the intensity of the newly detected longitudinal artifact, and compares the intensity of the newly detected longitudinal artifact with that of the previous longitudinal artifact.

The movement controller 2101 controls the movement mechanism 150 to move the OCT optical system in the same direction as the previous movement direction if the new intensity is higher than the previous intensity. On the other hand, the movement controller 2101 controls the movement mechanism 150 to move the OCT optical system in the opposite direction to the previous movement direction if the new intensity is lower than the previous intensity. The series of processes according to the present example may be terminated if there is no difference between the new intensity and the previous intensity (more generally, if the difference is smaller than a predetermined threshold).

Through iteratively performing such a series of processes, the position of the OCT optical system yielding a longitudinal artifact with a higher intensity may be searched for. The high intensity of the longitudinal artifact reflects the accuracy of the alignment of the OCT optical system with respect to the corneal apex. Therefore, the accuracy of the alignment of the OCT optical system with respect to the corneal apex may be enhanced by searching for the position of the OCT optical system at which a longitudinal artifact with a higher intensity can be acquired.

As a second example, the movement controller 2101 may be configured to execute control of the movement mechanism 150 so that a longitudinal artifact is located at the frame center of an OCT image. In other words, the movement controller 2101 may be configured to execute control of the movement mechanism 150 so that the artifact detected by the artifact detecting processor 232 passes through the center of the OCT image frame. Like the first example, the control of the present example may also be implemented by iteratively performing a series of processes including OCT image acquisition, longitudinal artifact detection, and movement of the OCT optical system.

As a specific example thereof, the series of processes as follows is executed in parallel with iterative application of an OCT scan of a predetermined pattern to the anterior segment to acquire time series OCT images. The artifact detecting processor 232 detects longitudinal artifacts in the OCT images sequentially acquired through the iterative application of the OCT scan. The movement controller 2101 (or, another element of the controller 210, the artifact detecting processor 232, or another element of the data processor 230; the same applies below) determines the positions of the detected longitudinal artifacts in the image frames of the OCT images.

The position of a longitudinal artifact in an image frame is, for example, the deviation of the longitudinal artifact with respect to a predetermined frame center. Here, considering that the longitudinal artifact has a shape along the A-scan direction (z direction), the frame center may be set to the center in at least one direction of at least the x direction and the y direction. For example, the center of the image frame in the x direction may be set to the frame center if the OCT image is a B-scan image along the x direction. The center of the image frame in the y direction may be set to the frame center if the OCT image is a B-scan image along the y direction. The center of the xy-plane in the image frame may be set to the frame center if the OCT image is a three dimensional image. The position corresponding to both the center in the x direction and the center in the y direction in the image frame may be set to the frame center if the OCT image is a B-scan obtained using a line scan of which the vector component in the x direction and the vector component in the y direction are both non-zero. As described here as examples, the frame center may be set according to the pattern and/or the direction of an OCT scan.

The movement controller 2101 controls the movement mechanism 150 to move the OCT optical system after the movement controller 2101 has determined the position of a longitudinal artifact in an image frame.

Subsequently, the artifact detecting processor 232 detects a longitudinal artifact in an OCT image acquired after the movement of the OCT optical system. The movement controller 2101 then determines the position of a new longitudinal artifact in the image frame of the OCT image newly acquired.

The position of a longitudinal artifact in an image frame can be represented by a deviation vector (displacement vector) of the longitudinal artifact with respect to the center of the image frame. The movement controller 2101 calculates the inverse vector of the deviation vector, and controls the movement mechanism 150 to move the OCT optical system in the direction and by the distance both corresponding to the inverse vector calculated.

The series of such processes may be repeated so that the magnitude of the deviation vector becomes stable below a predetermined threshold. The series of processes is an example of tracking. This makes it possible to acquire an OCT image in which the corneal apex is located at the center of the frame.

The two examples described above (the first example and the second example) may be performed in parallel with one another. This configuration makes it possible to acquire an OCT image in which the corneal apex is located at the center of the frame while improving the alignment accuracy of the OCT optical system with respect to the corneal apex.

<Corneal Image Detecting Processor 233>

The corneal image detecting processor 233 analyzes the OCT image constructed by the image constructing unit 220 to detect a corneal image. The corneal image detection may be executed based on a predetermined feature (characteristic) such as brightness, a position, and a shape, as in the case with the longitudinal artifact detection described above. The corneal image detection may include image processing such as segmentation.

The corneal image may be an entire image region corresponding to the cornea depicted in the OCT image, or only a part of this image region. For example, when the B-scan image 600 shown in FIG. 5 is processed, the corneal image detecting processor 233 may detect any one or more of the followings: the entire corneal cross sectional image, which is a high brightness image region having a shape similar to part of an annulus; the upper edge (corneal front surface, anterior corneal surface) of the corneal cross sectional image; the apex of the anterior corneal surface (corneal apex); the lower edge (corneal back surface, posterior corneal surface); the apex of the posterior corneal surface; and a sub-tissue of the cornea (corneal epithelium, Bowman's membrane, corneal stroma, Dua's layer, Descemet's membrane, corneal endothelium).

In the case where the corneal image detecting processor 233 is capable of detecting the corneal apex, the corneal apex detection may be performed before the longitudinal artifact detection and the result of the corneal apex detection may be provided to the artifact detecting processor 232. The artifact detecting processor 232 may execute the longitudinal artifact detection based on the result of the corneal apex detection carried out by the corneal image detecting processor 233.

<Position Judging Processor 234>

The position judging processor 234 judges whether a common region (an intersection) between the longitudinal artifact detected by the artifact detecting processor 232 and the corneal image detected by the corneal image detecting processor 233 is located within a predetermined area in an image frame.

The area (allowable area) in the image frame that serves as a reference (criterion) for the position judgement process may be set in advance, or may be set for each OCT image. As an example of the latter, the allowable area may be set based on the size of the corneal image depicted in the OCT image.

As described above, when iteratively applying an OCT scan of a predetermined pattern to the anterior segment to acquire time series OCT images, the artifact detecting processor 232 and the corneal image detecting processor 233 perform their respective analyses on the same OCT image. These analyses are executed in parallel, for example. As a result of these analyses, both a longitudinal artifact and a corneal image are detected from a single OCT image. The allowable area described above is set in this OCT image.

The position judging processor 234 identifies the intersection between the detected longitudinal artifact and the detected corneal image. As described above, a longitudinal artifact is a band shaped image region along the A-scan direction (z direction), and a corneal image is typically an upwardly convex image region of an annular shape, and further a longitudinal artifact occurs in such a way that it passes through the corneal apex and its vicinity. According to these conditions, when the corneal apex and/or its vicinity are depicted in an OCT image, in other words, when a longitudinal artifact is depicted in the OCT image, the longitudinal artifact and the corneal image cross each other at the corneal apex and/or its vicinity. This intersecting region, more specifically, the region in which the longitudinal artifact and the corneal image overlap is set to the intersection. The position judging processor 234 may compare a pixel group representing the longitudinal artifact and a pixel group representing the corneal image with each other, thereby identifying one or more pixels included in both of these two pixel groups and setting the one or more pixels to the intersection.

Furthermore, the position judging processor 234 judges whether or not the intersection identified is included in the allowable area. This judgement process is, for example, carried out by making a judgement whether at least part of the one or more pixels forming the intersection are included in the allowable area. Alternatively, the judgement process may be carried out by making a judgement whether all of the one or more pixels forming the intersection are included in the allowable area.

Figure 6:
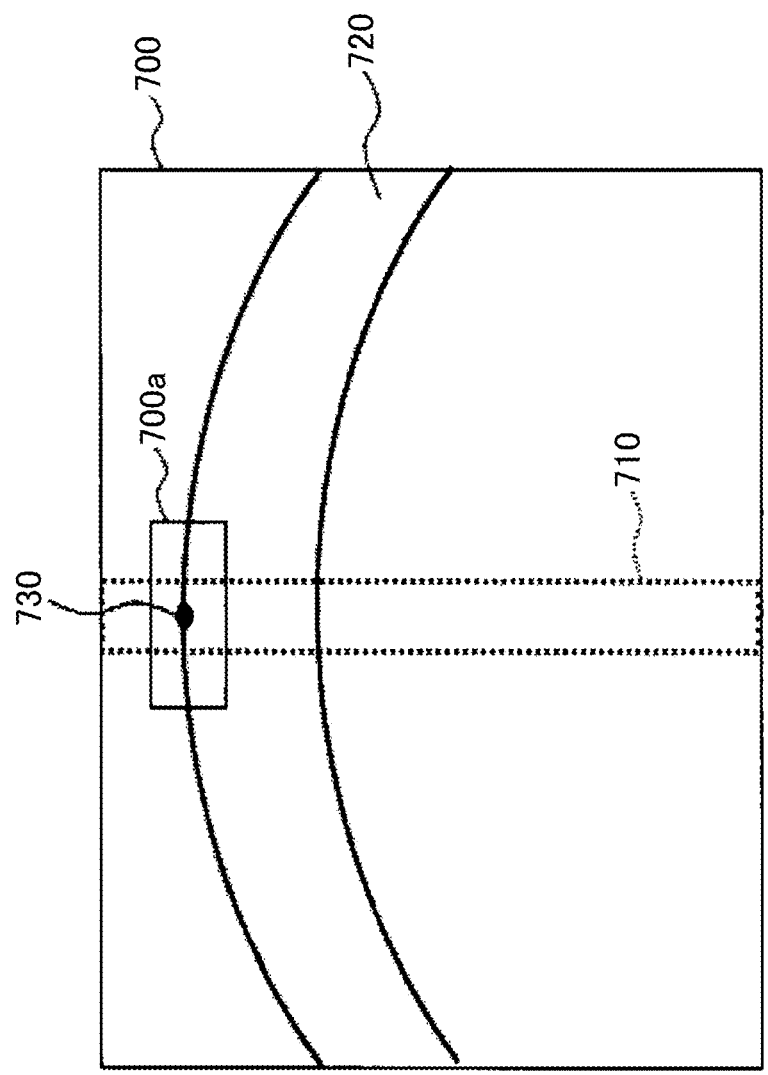
FIG. 6 is a schematic diagram for describing an operation that can be performed by the ophthalmic apparatus according to the embodiment example.

In the case where the B-scan image 700 illustrated in FIG. 6 is used for the position judgement process, the artifact detecting processor 232 analyzes the B-scan image 700 to detect the longitudinal artifact 710, and the corneal image detecting processor 233 analyzes the B-scan image 700 to detect the corneal image 720 (or part of the corneal image 720). The allowable area 700a has been set in the B-scan image 700.

The position judging processor 234 detects the corneal apex from the corneal image 720, and identifies the intersection 730 between the detected corneal apex and the longitudinal artifact 710. Further, the position judging processor 234 judges whether or not the identified intersection 730 is included in the allowable area 700a. In the example shown in FIG. 6, the intersection 730 is located inside the allowable area 700a. On the other hand, the intersection 730 may be located outside the allowable area 700a if the relative position between the subject's eye E and the OCT optical system at the moment when the B-scan image 700 is obtained is inappropriate.

Note that while such position judgement is executed after the movement control of the OCT optical system based on the longitudinal artifact in the OCT image (described above), the relative position between the subject's eye E and the OCT optical system constantly changes because of the eye movement of the subject's eye E even after the movement control has been executed. Therefore, making a judgement regarding whether or not the intersection of the longitudinal artifact and the corneal image is located within the allowable area is important in order to obtain an appropriate OCT image.

The condition of the intersection of the longitudinal artifact and the corneal image being included in the allowable area is a necessary condition in the present embodiment example for applying an OCT scan to the anterior segment to acquire data (e.g., an image, a measurement value) used for diagnosis.

<Image Quality Evaluating Processor 235>

The image quality evaluating processor 235 calculates an image quality evaluation value of the OCT image constructed by the image constructing unit 220. The image quality evaluation value is a numerical value indicating the degree of the image quality of the OCT image, and is used to evaluate whether or not the image quality is adequate.

An image quality evaluation value may be any type of numerical value that can be calculated by using any method or technique. A typical image quality evaluation value is a signal to noise ratio (SN ratio) regarding two types of image regions in an OCT image. A specific example of such an image quality evaluation value is an SN ratio regarding a signal in an image region representing a site of an eye (anterior segment) and a noise in an image region representing a background that is not a site of the eye. An image region representing a site of an anterior segment will be referred to as an anterior segment region, and an image region representing a background will be referred to as a background region.

Arbitrary method or technique may be employed to calculate an image quality evaluation value represented as an SN ratio for an anterior segment region and a background region. A specific example thereof will be described below.

First, the image quality evaluating processor 235 identifies a pixel with the maximum brightness and a pixel with the minimum brightness, for each of the plurality of A-scan images forming the OCT image. Next, the image quality evaluating processor 235 creates a histogram of brightness values (e.g., of 8-bit) based on the brightness values of a pixel group in a predetermined area that includes the pixel with the maximum brightness identified (e.g., based on the brightness values of 40 pixels around (before and after) the maximum brightness pixel). Similarly, the image quality evaluating processor 235 creates a histogram of the brightness values based on the brightness values of a pixel group in a predetermined area that includes the pixel with the minimum brightness identified.

Subsequently, the image quality evaluating processor 235 searches for the maximum position (brightness value) whose frequency of occurrence exceeds zero in the histogram corresponding to the pixel group that includes the pixel with the minimum brightness. Further, in the histogram corresponding to the pixel group that includes the pixel with the maximum brightness, the image quality evaluating processor 235 determines: a total number of pixels (N) included in the range equal to or less than the brightness values searched for in the above process; and a total number of pixels (S) included in the 255th brightness value from above the brightness value searched for. Then, the image quality evaluating processor 235 evaluates the percentage of the image that can be considered as a signal (i.e., the portion of the image that can be considered as not being a noise) using the following formula: 100×S÷(S+N). The image quality evaluating processor 235 applies the series of operations (calculations) described above to each A-scan image, thereby obtaining a plurality of numerical values corresponding to the plurality of A-scan images. The image quality evaluating processor 235 then calculates the average value of these numerical values and sets the average value to the image quality evaluation value.

The image quality evaluating processor 235 (or, another element of the data processor 230 or the controller 210) may judge whether the image quality evaluation value calculated is equal to or greater than a predetermined threshold. The threshold may be a default value or a value set according to an arbitrary attribute or an arbitrary condition. The image quality of the OCT image is judged to be adequate if the image quality evaluation value is equal to or greater than the threshold. On the other hand, the image quality of the OCT image is judged to be inadequate if the image quality evaluation value is less than the threshold.

The condition of the image quality evaluation value being equal to or greater than the threshold is a necessary condition in the present embodiment example for applying an OCT scan to the anterior segment to acquire data (e.g., an image, a measurement value) used for diagnosis.

The image quality evaluation value calculated by the image quality evaluating processor 235 and/or an evaluation result (judgement result) based thereon may be utilized for processing and/or control. Typically, the image quality evaluation value or the evaluation result may be utilized for processing and control for improving the image quality of an OCT image.

A specific example thereof will be described. The polarization controller 2103 may be configured to control the polarization device 118 (and/or the polarization device 103)

to increase the image quality evaluation value calculated by the image quality evaluating processor 235. The control of the present example may be implemented by iteratively performing a series of processes including the acquisition of an OCT image, the calculation of an image quality evaluation value, the evaluation of an image quality, and the control of the polarization device 118, for example.

<Artifact Eliminating Processor 236>

The artifact eliminating processor 236 eliminate the longitudinal artifact detected, by the artifact detecting processor 232, from the OCT image constructed by the image constructing unit 220. The display controller 2104 may control the display device 241 to display the OCT image obtained through the longitudinal artifact elimination performed by the artifact eliminating processor 236.

In the artifact eliminating process, the values of the pixel group corresponding to the longitudinal artifact are replaced with other values. For example, the artifact eliminating processor 236 may obtain a new value of a target pixel based on the values of one or more pixels located around the target pixel. Such processing includes, for example, any known filtering.

The display controller 2104 may display, on the display device 241, the OCT image in which the values of the pixel group corresponding to the longitudinal artifact have been converted.

<Operation>

Figure 7A:
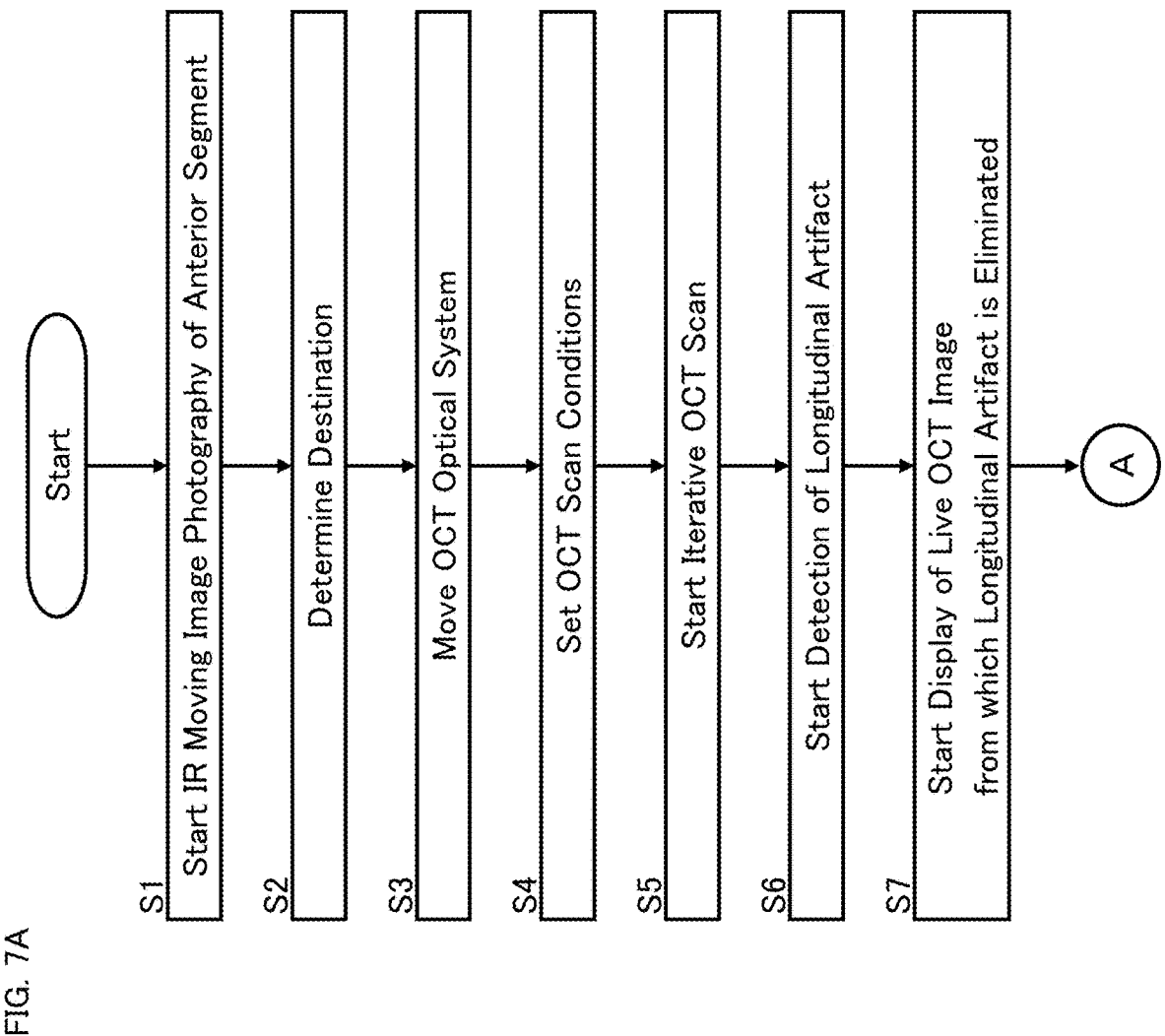
FIG. 7A is a flowchart illustrating an operation that can be performed by the ophthalmic apparatus according to the embodiment example.
Figure 7B:
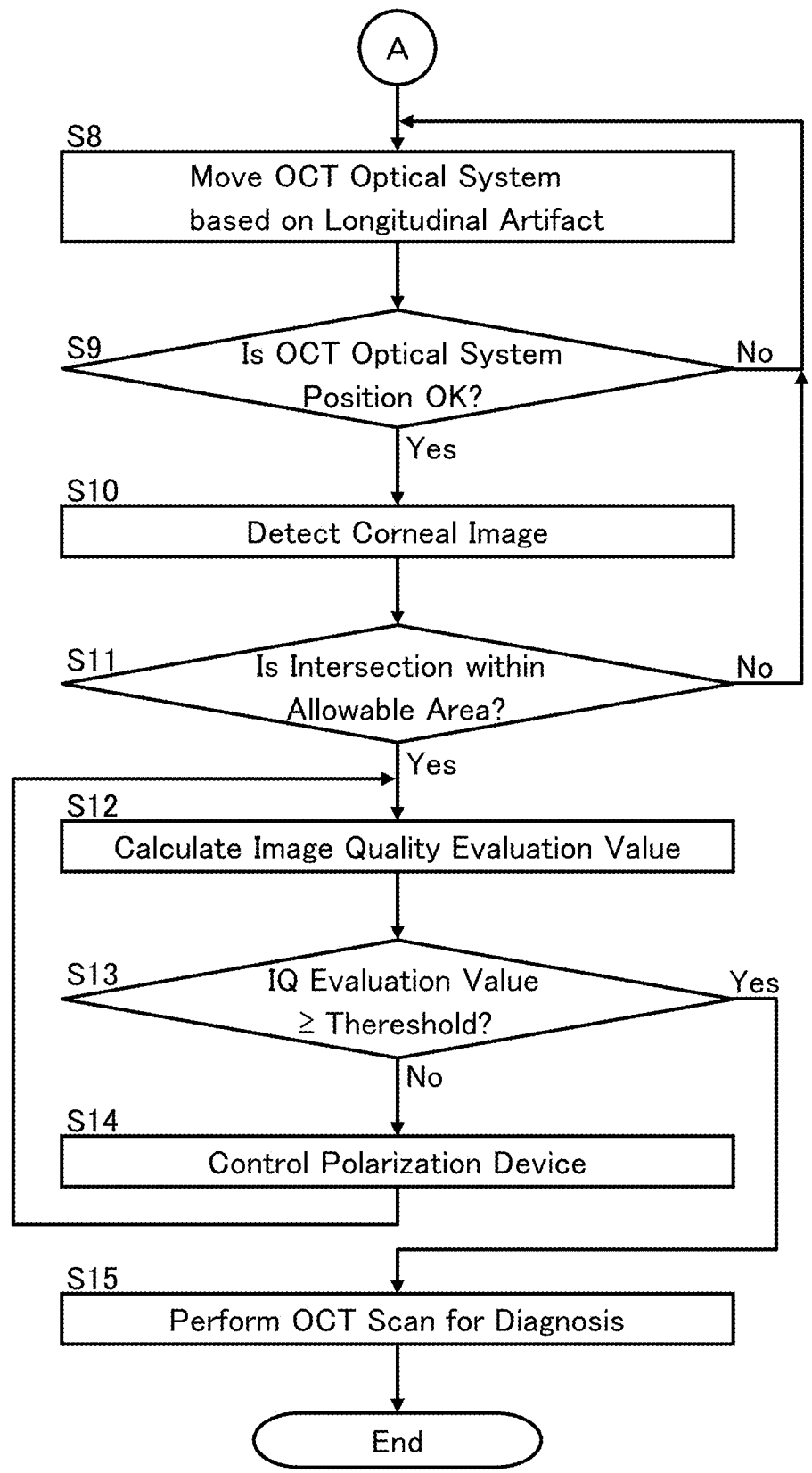
FIG. 7B is a flowchart illustrating an operation that can be performed by the ophthalmic apparatus according to the embodiment example.

An operation of the ophthalmic apparatus 1 according to the present embodiment example will be described. FIG. 7A and FIG. 7B show an example of the operation of the ophthalmic apparatus 1.

(S1: Start Infrared Moving Image Photography of Anterior Segment)

To begin with, the fundus camera unit 2 of the ophthalmic apparatus 1 starts the infrared moving image photography of the anterior segment of the subject's eye E. Frames acquired by the infrared moving image photography (anterior segment images) are transferred to the data processor 230 via the controller 210. The transfer is executed as real-time processing.

(S2: Determine Destination)

The destination determining processor 231 analyzes the anterior segment image transferred from the fundus camera unit 2 to determine a destination of the OCT optical system. Typically, the destination determining processor 231 may detect the pupil center from the anterior segment image, and set the detected pupil center to the destination. Such processing is, for example, real-time processing executed for each of the anterior segment images transferred from the fundus camera unit 2.

(S3: Move OCT Optical System)

The movement controller 2101 moves the OCT optical system by controlling the movement mechanism 150 based on the destination determined in the step S2. Typically, the movement controller 2101 moves the OCT optical system such that the optical axis of the OCT optical system passes through the pupil center. This movement control is executed as real-time processing.

(S4: Set OCT Scan Conditions)

The scan controller 2102 sets conditions to be applied to the iterative OCT scan (repetitive OCT scan, repetition OCT scan) that will be started in the next step S5. Typically, the scan controller 2102 sets a pattern of the OCT scan and also sets an area to which the OCT scan is applied such that the center of the scan pattern (scan center) is located at the pupil center (for example, see FIG. 4C).

(S5: Start Iterative OCT Scan)

The scan controller 2102 starts the iterative OCT scan under the conditions set in the step S4.

An iterative OCT scan is typically a scan mode in which an OCT scan of the same pattern is iteratively (repeatedly) applied to the anterior segment, whereby time series OCT images are acquired. The time series OCT images are used for preparatory operations such as alignment and image quality tuning.

An iterative OCT scan is typically a scan mode of iteratively (repeatedly) performing the same B-scan whose scan center is located at the optical axis position of the OCT optical system. According to such an iterative B-scan, it is possible to apply the B-scans passing through the pupil center or the vicinity thereof (and thus, passing through the corneal apex or the vicinity thereof) at a high repetition frequency.

Note that any scan pattern, such as a cross scan, a multi-cross scan, a radial scan, or a three dimensional scan, may be employed to facilitate the search for the corneal apex where longitudinal artifacts occur.

The selection of a scan pattern employed for an iterative OCT scan may be made in consideration of various kinds of conditions such as a repetition frequency, the load and/or the time required for data processing, and/or the degree of easiness of corneal apex search. Further, a plurality of conditions may be met by changing or switching the pattern of the iterative OCT scan and/or the size of the scan area during the process.

An iterative OCT scan yields data sets acquired through respective OCT scans. The image constructing unit 220 constructs a plurality of OCT images based respectively on a plurality of data sets sequentially acquired by the iterative OCT scan. When performing an iterative B-scan, a plurality of data sets is sequentially acquired in accordance with the repetition of the B-scan. The image constructing unit 220 constructs a plurality of B-scan images based respectively on the plurality of data sets.

(S6: Start Detection of Longitudinal Artifact)

The artifact detecting processor 232 analyzes each of the plurality of OCT images (or, each of only part of the plurality of OCT images) sequentially acquired in the step S5, to detect a longitudinal artifact in each of the OCT images. This processing is executed as real-time processing.

(S7: Start Display of Live OCT Image from which Longitudinal Artifact is Eliminated)

The artifact eliminating processor 236 eliminates the detected longitudinal artifact from each (or part) of the plurality of OCT images sequentially acquired in the step S5. This artifact elimination is performed as real-time processing.

The display controller 2104 controls the display device 241 to display the OCT image from which the longitudinal artifact has been eliminated. Typically, the display controller 2104 displays, as a moving image, the time series OCT images sequentially created by the artifact eliminating processor 236. The display control is executed as real-time processing. With this, a live OCT image, which is free of longitudinal artifacts, can be provided.

(S8: Move OCT Optical System Based on Longitudinal Artifact)

The movement controller 2101 moves the OCT optical system by controlling the movement mechanism 150 based on each of the plurality of longitudinal artifacts (or part of the plurality of longitudinal artifacts) sequentially detected in the step S6.

Typically, the movement controller 2101 adjust the position of the OCT optical system so that the intensity of the longitudinal artifact generated in the OCT image is maximized, and/or, so that the longitudinal artifact is located at the frame center of the OCT image.

(S9: Is OCT Optical System Position OK?)

The movement controller 2101 judges whether the position of the OCT optical system after the movement of the step S8 meets a predetermined condition. A criterion or reference for judgement typically relates to the intensity of the longitudinal artifact and/or the deviation of the longitudinal artifact from the frame center of the OCT image.

The process proceeds to the step S10 if the position of the OCT optical system meets the predetermined condition (S9: Yes).

The process returns to the step S8 if the position of the OCT optical system does not meet the predetermined condition (S9: No), and then the steps S8 and S9 are repeated until the predetermined condition is met. Note that the ophthalmic apparatus 1 may be configured to issue an error if the steps S8 and S9 have been repeated a predetermined number of times or have been repeated for a predetermined duration of time.

(S10: Detect Corneal Image)

The corneal image detecting processor 233 analyzes each of the plurality of OCT images (or part of the plurality of OCT images) sequentially acquired in the step S5, to detect a corneal image (e.g., a corneal apex) from each of the plurality of OCT images. This processing is executed as real-time processing.

(S11: Is Intersection within Allowable Area?)

The position judging processor 234 identifies an intersection of the longitudinal artifact detected in the step S6 and the corneal image detected in the step S10, and judges whether the intersection is located within the allowable area in the frame of that OCT image.

The process proceeds to the step S12 if the position judging processor 234 judges that the intersection is located within the allowable area (S11: Yes).

The process returns to the step S8 if the position judging processor 234 judges that the intersection is not located inside the allowable area (S11: No). Then, the steps S8 to S11 are repeated until "Yes" is issued as a judgement in both the steps S9 and S11. Note that the ophthalmic apparatus 1 may be configured to issue an error if part or all of the steps S8 to S11 have been repeated a predetermined number of times or have been repeated for a predetermined duration of time.

(S12: Calculate Image Quality Evaluation Value)

The image quality evaluating processor 235 analyzes each of the plurality of OCT images (or part of the plurality of OCT images) sequentially acquired in the step S5, to calculate an image quality evaluation value for each of the OCT images. This processing is executed as real-time processing.

(S13: Is Image Quality Evaluation Value Equal to or Greater than Threshold?)

The image quality evaluating processor 235 judges whether the image quality evaluation value calculated in the step S12 is equal to or greater than a predetermined threshold.

The process proceeds to the step S15 if the image quality evaluating processor 235 judges that the image quality evaluation value is equal to or greater than the predetermined threshold (S13: Yes).

The process proceeds to the step S14 if the image quality evaluating processor 235 judges that the image quality evaluation value is less than the predetermined threshold (S13: No).

(S14: Control Polarization Device)

If the image quality evaluating processor 235 judges that the image quality evaluation value is less than the predetermined threshold (S13: No), the polarization controller 2103 controls the polarization device 118 (and/or the polarization device 103) to increase the image quality evaluation value to be calculated next in the step S12.

The steps S12 to S14 are repeated until "Yes" is issued as a judgement in the step S13. Note that the ophthalmic apparatus 1 may be configured to issue an error if the steps S12 to S14 have been repeated a predetermined number of times or have been repeated for a predetermined duration of time.

(S15: Perform OCT Scan for Diagnosis)

As described above, if the image quality evaluating processor 235 judges that the image quality evaluation value is equal to or greater than the predetermined threshold (S13: Yes), then the step S15 is started. At this stage, the alignment state of the OCT optical system with respect to the anterior segment (the corneal apex, the pupil center, etc.) and the image quality of the OCT image to be acquired are adequate.

The scan controller 2102 applies an OCT scan to the anterior segment at the timing when such adequate conditions are secured. The image constructing unit 220 then constructs an OCT image from the data acquired by the OCT scan applied. The data processor 230 may also process and/or analyze this OCT image.

The OCT image acquired in the step S15 is typically used for diagnosis, and its scan condition is generally different from the condition for the iterative OCT scan started in the step S5. Typically, the OCT image obtained in the step S15 has higher definition. Further, arbitrary conditions of the OCT image obtained in the step S15 such as the scan pattern and/or the size of the scan area may be different from those of the iterative OCT scan started in the step S5.

With the above, the operation illustrated in FIG. 7A and FIG. 7B ends (End).

<Effects>

Some effects of the ophthalmic apparatus 1 according to the embodiment example will be described.

The ophthalmic apparatus 1 includes an OCT optical system, the image constructing unit 220, the artifact detecting processor 232, the movement mechanism 150, the movement controller 2101, the corneal image detecting processor 233, the position judging processor 234, the image quality evaluating processor 235, and the scan controller 2102.

The OCT optical system is an optical system configured for applying an OCT scan to the anterior segment of the subject's eye E. The OCT optical system in the embodiment example described above includes at least the series of elements forming the measurement arm in the fundus camera unit 2. The image constructing unit 220 is configured to construct an OCT image based on data acquired by the OCT scan.

The artifact detecting processor 232 is configured to analyze the OCT image constructed by the image constructing unit 220 to detect a longitudinal artifact. The longitudinal artifact is an artifact along an A-scan direction.

The movement mechanism 150 is configure to move (only a part of or all of) the OCT optical system. The movement controller 2101 (a first movement controller) is configured to perform control of the movement mechanism 150 based on the longitudinal artifact detected by the artifact detecting processor 232, to move the OCT optical system.

The corneal image detecting processor 233 is configured to analyze the OCT image constructed by the image constructing unit 220, to detect a corneal image.

The position judging processor 234 is configured make a judgement whether an intersection between the longitudinal artifact detected by the artifact detecting processor 232 and the corneal image detected by the corneal image detecting processor 233 is located within a predetermined area in a frame of the OCT image.

The image quality evaluating processor 235 is configured to calculate an image quality evaluation value of the OCT image constructed by the image constructing unit 220. For example, the image quality evaluating processor 235 may calculate, as an image quality evaluation value, a ratio between a signal in the anterior segment region and a noise in the background region in the OCT image constructed by the image constructing unit 220.

The scan controller 2102 is configured to perform control of the OCT optical system to apply an OCT scan of a predetermined pattern to the anterior segment, if the position judging processor 234 judges that the intersection is located within the predetermined area in the frame and also if the image quality evaluation value calculated by the image quality evaluating processor 235 is equal to or greater than a predetermined threshold.

According to the ophthalmic apparatus 1 configured in this way, preparatory operations can be carried out automatically while checking whether or not necessary conditions are met, and an OCT scan (imaging, measurement, etc.) can be executed at an appropriate timing at which the necessary conditions are met. The preparatory operations here include, for example, the alignment of the OCT optical system with respect to a target site, the adjustment of a depiction position of a target site in an image frame, and the control of the image quality.

Having automated the preparatory operations for applying an OCT scan to the anterior segment of a living eye in this way, even a person unfamiliar with the operation of the ophthalmic apparatus can easily conduct an OCT examination. This also makes it possible for a subject to have an OCT examination alone. As a result, the burdens on the subject and the examiner in the OCT examination is reduced.

In recent years, there is a movement to install an ophthalmic apparatus, to which an OCT technique and technology are applied, in an optician's store, a drug store, or a patient's home in order to use the apparatus for screening of eye diseases. The ophthalmic apparatus 1 in which the preparatory operations are automated is effective also as an ophthalmic apparatus to be installed in such places.

The ophthalmic apparatus 1 may be configured to execute the following series of processes after the movement controller 2101 (the first movement controller) has performed the control of the movement mechanism 150 based on the longitudinal artifact. First, the OCT optical system applies an OCT scan to the anterior segment. Next, the image constructing unit 220 constructs an OCT image based on data acquired by the OCT scan. Subsequently, the artifact detecting processor 232 analyzes the OCT image to detect a longitudinal artifact. Next, the corneal image detecting processor 233 analyzes the OCT image to detect a corneal image. Then, the position judging processor 234 judges whether an intersection of the longitudinal artifact and the corneal image is located within a predetermined area in a frame of the OCT image.

According to the ophthalmic apparatus 1 configured in this way, another OCT scan can be performed to construct an OCT image after alignment has been performed based on the longitudinal artifact, and then make a judgement on a depiction position of a target site based on the longitudinal artifact and the corneal image both detected from the OCT image. In other words, the ophthalmic apparatus 1 is capable of making a depiction position judgement under an adequate alignment condition achieved by the alignment on the basis of the longitudinal artifact. As a result, smooth linkage between the alignment and the depiction position judgement can be achieved.

The ophthalmic apparatus 1 may be configured in such a manner that the image quality evaluating processor 235 performs the calculation of an image quality evaluation value after the position judging processor 234 has judged that the intersection is located within the predetermined area.

According to the ophthalmic apparatus 1 configured in this way, the depiction position judgement can be made under an adequate alignment condition achieved by the alignment on the basis of the longitudinal artifact and the image quality evaluation can be performed after the adequate depiction position has been achieved. As a result, smooth linkage between the alignment, the depiction position judgement, and the image quality evaluation can be achieved.

The ophthalmic apparatus 1 includes the fundus camera unit 2 (an anterior segment photographing system) and the destination determining processor 231. The fundus camera unit 2 is configured to perform photography of the anterior segment. The destination determining processor 231 is configured to analyze an anterior segment image acquired by the fundus camera unit 2 to determine a destination of the OCT optical system. The movement controller 2101 (a second movement controller) is configured to perform control of the movement mechanism 150 based on the destination determined by the destination determining processor 231. The OCT optical system starts the application of an OCT scan to the anterior segment after the movement controller 2101 has performed the control of the movement mechanism 150.

According to the ophthalmic apparatus 1 configured in this way, (rough) alignment can be performed based on an anterior segment image before the application of the OCT scan. This facilitates alignment on the basis of the longitudinal artifact performed after the commencement of the OCT scan. This also enables smooth linkage between the alignment based on the anterior segment image and the alignment based on the longitudinal artifact.

The destination determining processor 231 may set the destination at a pupil center of the anterior segment for the alignment on the basis of the anterior segment image. The OCT optical system may start the application of an OCT scan of a pattern with a scan center located at the pupil center.

According to the ophthalmic apparatus 1 thus configured, the OCT scan can be started with the pupil center, which is one of the landmarks of the anterior segment, as a reference. This makes it possible to facilitate and expedite the alignment on the basis of the longitudinal artifact performed after the commencement of the OCT scan. More specifically, starting the OCT scan with the pupil center as a reference makes it easier to detect a longitudinal artifact occurring at the corneal apex and its vicinity, and thus facilitates and speeds up the alignment on the basis of the longitudinal artifacts.

The OCT scan performed by the OCT optical system after the alignment based on the anterior segment image may be an iterative OCT scan of a pattern with a scan center located at the pupil center. The image constructing unit 220 constructs a plurality of images based respectively on a plurality of data sets sequentially acquired by the iterative OCT scan. Note that the iterative OCT scan may be an iterative B-scan. Further, the OCT optical system may continue the iterative OCT scan at least until the image quality evaluating processor obtains an image quality evaluation value equal to or greater than the predetermined threshold.

According to the ophthalmic apparatus 1 configured in this way, a plurality of OCT images (time series OCT images) synchronized with the iteration of the OCT scan can be obtained. The time series OCT images may be employed and utilized for various purposes such as alignment operation, depiction position judgement processing, image quality evaluation processing, and moving image display operation.

In the alignment based on the longitudinal artifact, the movement controller 2101 (the first movement controller) can perform the control of the movement mechanism 150 to increase (enhance) the intensity of the longitudinal artifact detected by the artifact detecting processor 232.

According to the ophthalmic apparatus 1 configured in this way, the accuracy of the alignment of the OCT optical system with respect to the corneal apex can be increased by searching for a position of the OCT optical system at which a longitudinal artifact with a higher intensity can be obtained.

In the alignment based on the longitudinal artifact, the movement controller 2101 (the first movement controller) can perform the control of the movement mechanism 150 such that the artifact detected by the artifact detecting processor 232 passes through the center of the image frame.

According to the ophthalmic apparatus 1 configured in this way, the alignment of the OCT optical system can be performed in such a manner that the corneal apex is depicted at an appropriate position in the image frame.

The OCT optical system includes the measurement arm and the reference arm. The measurement arm is configured to guide the measurement light LS to the anterior segment, and the reference arm is configured to guide the reference light LR that is to be superposed on return light of the measurement light LS returning from the anterior segment. At least one of the measurement arm and the reference arm may include a polarization device. The polarization device is configured to change a polarization state (polarization condition) of the light guided thereby. The ophthalmic apparatus 1 includes the polarization device 118 that is provided in the reference arm. The ophthalmic apparatus 1 may further include the polarization controller 2103. The polarization controller 2103 is configured to perform control of the polarization device to increase the image quality evaluation value calculated by the image quality evaluating processor 235 (e.g., the ratio between the signal in the anterior segment region and the noise in the background region).

According to the ophthalmic apparatus 1 configured as described above, an image quality of an OCT image can be improved if the image quality is low.

The ophthalmic apparatus 1 may include the display controller 2104 configured to display the OCT image constructed by the image constructing unit 220 on the display device 241 (a display device). The display device may be included in the ophthalmic apparatus 1 or may be a peripheral device connected to the ophthalmic apparatus 1.

According to the ophthalmic apparatus 1 thus configured, it is possible to offer the user a visualization of the OCT image constructed by the image constructing unit 220.

The ophthalmic apparatus 1 may include the artifact eliminating processor 236. The artifact eliminating processor 236 is configured to eliminate the longitudinal artifact detected, by the artifact detecting processor 232, from the OCT image constructed by the image constructing unit 220. Note that the artifact eliminating processor 236 may also be capable of eliminating an artifact other than the longitudinal artifact. The display controller 2104 may display, on the display device 241, the OCT image from which at least the longitudinal artifact is eliminated by the artifact eliminating processor 236. Note that the artifact eliminating processor 236 and the display controller 2104 are included in the "display controller".

According to the ophthalmic apparatus 1 configured in this way, a longitudinal artifact, which is useful for alignment but is an obstacle to observation, can be eliminated from a display image.

<Control Method of Ophthalmic Apparatus, Program, Recording Medium>

The embodiment examples described above also provide a method of controlling an ophthalmic apparatus. The ophthalmic apparatus to which this control method can be applied includes an OCT optical system that applies an OCT scan to an anterior segment of a subject's eye, an image constructing unit that constructs an image based on data acquired by the OCT scan, and a movement mechanism that moves the OCT optical system.

The control method of the present embodiment example includes an artifact detecting step, a movement control step, a corneal image detecting step, a position judging step, an image quality evaluating step, and a scan control step.

The artifact detecting step detects an artifact along an A-scan direction by analyzing the image constructed by the image constructing unit. The movement control step performs control of the movement mechanism based on the artifact detected. The corneal image detecting step detects a corneal image by analyzing the image constructed by the image constructing unit. The position judging step judges whether an intersection of the artifact detected and the corneal image detected is located within a predetermined area in an image frame. The image quality evaluating step calculates an image quality evaluation value of the image constructed by the image constructing unit. The scan control step performs control of the OCT optical system to apply an OCT scan of a predetermined pattern to the anterior segment, if it is judged that the intersection is located within the predetermined area and the image quality evaluation value calculated is equal to or greater than a predetermined threshold.

Any of the processes that can be executed by the ophthalmic apparatus 1 according to the above embodiment example, can be combined with the control method of the present embodiment example.

According to such a control method, the same effects are achieved as those of the ophthalmic apparatus 1 according to the embodiment example described above.

It is possible to configure a program that causes the ophthalmic apparatus to execute such a control method. The program may include, for example, any of the programs described regarding the ophthalmic apparatus 1 according to the embodiment example described above.

Also, it is possible to create a computer-readable non-transitory recording medium storing such a program. The non-transitory recording medium may be in any form, and examples thereof include a magnetic disk, an optical disk, a magneto-optical disk, a semiconductor memory, and the like.

The aspects described above are merely illustrative of the implementation of the present invention. A person who intends to implement the present invention may apply any modification (omission, substitution, replacement, addition, etc.) to the above aspects.

While certain embodiments have been described, these embodiments have been presented by way of example only, and are not intended to limit the scope of the inventions. Indeed, the novel embodiments described herein may be embodied in a variety of other forms; furthermore, various omissions, substitutions, additions and changes in the form of the embodiments described herein may be made without departing from the spirit of the inventions. The accompanying claims and their equivalents are intended to cover such forms or modifications as would fall within the scope and spirit of the inventions.

What is claimed is:

1. An ophthalmic apparatus comprising:
an optical coherence tomography (OCT) optical system configured to apply an OCT scan to an anterior segment of an eye;
processing circuitry configured as an image constructing unit configured to construct an image based on data acquired by the OCT scan;
the processing circuitry further configured as an artifact detecting unit configured to analyze the image constructed by the image constructing unit to detect an artifact along an A-scan direction;
a movement mechanism including an actuator and configured to move the OCT optical system;
the processing circuitry further configured as a first movement controller configured to perform control of the movement mechanism based on the artifact detected by the artifact detecting unit;
the processing circuitry further configured as a conical image detecting unit configured to analyze the image constructed by the image constructing unit to detect conical image;
the processing circuitry further configured as a position judging unit configured to judge whether an intersection of the artifact detected by the artifact detecting unit and the corneal image detected by the corneal image detecting unit is located within a predetermined area in an image frame;
the processing circuitry further configured as an image quality evaluating unit configured to calculate an image quality evaluation value of the image constructed by the image constructing unit; and
the processing circuitry further configured as a scan controller configured to perform control of the OCT optical system to apply an OCT scan of a predetermined pattern to the anterior segment, if the position judging unit judges that the intersection is located within the predetermined area and the image quality evaluation value calculated by the image quality evaluating unit is equal to or greater than a predetermined threshold.

2. The ophthalmic apparatus of claim 1, wherein after the first movement controller performs the control of the movement mechanism,
the OCT optical system applies an OCT scan to the anterior segment,
the image constructing unit constructs an image based on data acquired by the OCT scan,
the artifact detecting unit analyzes the image to detect an artifact;
the corneal image detecting unit analyzes the image to detect a corneal image, and
the position judging unit judges whether an intersection of the artifact and the corneal image is located within a predetermined area in a frame of the image.

3. The ophthalmic apparatus of claim 2, wherein the image quality evaluating unit performs calculation of an image quality evaluation value after the position judging unit judges whether the intersection is located within the predetermined area.

4. The ophthalmic apparatus of claim 2, wherein the processing circuitry is further configured as:
an anterior segment photographing system configured to photograph the anterior segment;
a destination determining unit configured to analyze an anterior segment image acquired by the anterior segment photographing system to determine a destination of the OCT optical system; and
a second movement controller configured to perform control of the movement mechanism based on the destination determined by the destination determining unit,
wherein the OCT optical system starts application of an OCT scan to the anterior segment after the second movement controller performs the control of the movement mechanism.

5. The ophthalmic apparatus of claim 4, wherein
the destination determining unit sets the destination at a pupil center of the anterior segment, and
the OCT optical system starts application of an OCT scan of a pattern with a scan center located at the pupil center.

6. The ophthalmic apparatus of claim 5, wherein
the OCT optical system starts application of an iterative OCT scan of a pattern with a scan center located at the pupil center, and
the image constructing unit constructs a plurality of images based respectively on a plurality of pieces of data sequentially acquired by the iterative OCT scan.

7. The ophthalmic apparatus of claim 6, wherein the iterative OCT scan includes an iterative B-scan.

8. The ophthalmic apparatus of claim 6, wherein the OCT optical system continues the iterative OCT scan at least until the image quality evaluating unit obtains an image quality evaluation value equal to or greater than the predetermined threshold.

9. The ophthalmic apparatus of claim 1, wherein the first movement controller performs the control of the movement mechanism to increase an intensity of an artifact detected by the artifact detecting unit.

10. The ophthalmic apparatus of claim 1, wherein the first movement controller performs the control of the movement mechanism such that an artifact detected by the artifact detecting unit passes through a center of an image frame.

11. The ophthalmic apparatus of claim 1, wherein the image quality evaluating unit calculates, as the image quality evaluation value, a ratio between a signal of an anterior segment region and a noise of a background region in the image constructed by the image constructing unit.

12. The ophthalmic apparatus of claim 11, wherein the OCT optical system includes a measurement arm and a reference arm, the measurement arm being configured to guide measurement light to the anterior segment, and the reference arm being configured to guide reference light that is superposed on return light of the measurement light returning from the anterior segment, wherein at least one of the measurement arm and the reference arm includes a polarization device that changes a polarization state of light guided thereby, and the ophthalmic apparatus further comprising a polarization controller circuit configured to perform control of the polarization device to increase the ratio calculated by the image quality evaluating unit.

13. The ophthalmic apparatus of claim 1, wherein the processing circuitry is further configured as a display controller configured to display the image constructed by the image constructing unit on a display device.

14. The ophthalmic apparatus of claim 13, wherein the display controller includes an artifact eliminating unit configured to eliminate the artifact detected by the artifact detecting unit from the image constructed by the image constructing unit, and displays on the display device an image obtained by eliminating the artifact by the artifact eliminating unit.

15. A method of controlling an ophthalmic apparatus including an optical coherence tomography (OCT) optical system that applies an OCT scan to an anterior segment of an eye, an image constructing unit that constructs an image based on data acquired by the OCT scan, and a movement mechanism that moves the OCT optical system, the method comprising:
  detecting an artifact along an A-scan direction by analyzing the image constructed by the image constructing unit;
  performing control of the movement mechanism based on the artifact detected;
  detecting a corneal image by analyzing the image constructed by the image constructing unit;
  judging whether an intersection of the artifact detected and the corneal image detected is located within a predetermined area in an image frame;
  calculating an image quality evaluation value of the image constructed by the image constructing unit; and
  performing control of the OCT optical system to apply an OCT scan of a predetermined pattern to the anterior segment, if the intersection is judged to be located within the predetermined area and the image quality evaluation value calculated is equal to or greater than a predetermined threshold.

16. A computer-readable non-transitory recording medium storing a program causing a computer to execute the method of claim 15.

17. A method of ophthalmic optical coherence tomography (OCT) comprising:
  applying an OCT scan to an anterior segment of an eye;
  constructing an image based on data acquired by the OCT scan;
  detecting an artifact along an A-scan direction by analyzing the image;
  performing alignment based on the artifact;
  detecting a corneal image by analyzing the image;
  judging whether an intersection of the artifact and the corneal image is located within a predetermined area in an image frame;
  calculating an image quality evaluation value of the image; and
  applying an OCT scan of a predetermined pattern to the anterior segment, if the intersection is judged to be located within the predetermined area and the image quality evaluation value is equal to or greater than a predetermined threshold.

18. A computer-readable non-transitory recording medium storing a program causing an ophthalmic apparatus to execute the method of claim 17.

* * * * *